(12) United States Patent
Mazaleyrat et al.

(10) Patent No.: US 10,113,186 B2
(45) Date of Patent: *Oct. 30, 2018

(54) ALKENOL DEHYDRATASE VARIANTS

(71) Applicants: Global Bioenergies, Evry (FR); Scientist of Fortune, S.A., Luxembourg (LU)

(72) Inventors: Sabine Mazaleyrat, Le Russey (FR); Marc Delcourt, Paris (FR); Philippe Marlière, Tournai (BE)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,248

(22) PCT Filed: Nov. 12, 2015

(86) PCT No.: PCT/EP2015/076450
§ 371 (c)(1),
(2) Date: May 11, 2017

(87) PCT Pub. No.: WO2016/075244
PCT Pub. Date: May 19, 2016

(65) Prior Publication Data
US 2017/0321229 A1 Nov. 9, 2017

(30) Foreign Application Priority Data
Nov. 13, 2014 (EP) .................................. 14193010

(51) Int. Cl.
*C12P 5/02* (2006.01)
*C12N 9/88* (2006.01)

(52) U.S. Cl.
CPC ............... *C12P 5/026* (2013.01); *C12N 9/88* (2013.01); *C12Y 402/01127* (2013.01)

(58) Field of Classification Search
CPC .................................. C12N 9/93; C12P 5/023
USPC .......................... 435/167, 183, 252.3, 320.1
See application file for complete search history.

(56) References Cited

FOREIGN PATENT DOCUMENTS

| WO | 2014015210 A2 | 1/2014 |
| WO | 2014184345 A1 | 11/2014 |

OTHER PUBLICATIONS

Anonymous, "Reviewed; 397 AA. RecName: Full =Linalool anonymousdehydratase/isomerase; EC=4.2.1.127; EC=5.4.4.4; AltName: Full=Geraniol isomerase; AltName: Full =Linalool dehydratase-isomerase; AltName: =Full=Myrcene hydratase", Uniprot, Nov. 30, 2010 (Nov. 30, 2010), XP002703976, the whole document.
Desantis et al., "Creation of a Productive, Highly Enantioselective Nitrilase through Gene Site Saturation Mutagenesis (GSSM) ", Journal of the American Chemical Society, American Chemical Society, vol. 125, No. 38, pp. 11476-11477, (2003).
International Search Report and Written Opinion dated Mar. 4, 2016 in PCT/EP2015/076450.
Reetz, et. al., "Iterative Saturation Mutagenesis Accelerates Laboratory Evolution of Enzyme Stereoselectivity: Rigorous Comparison with Traditional Methods", Journal of the American Chemical Society, vol. 132, No. 26, pp. 9144-9152, (2010).
International Preliminary Report on Patentability received in PCT/EP2015/076450 (dated May 26, 2017).
Communication pursuant to Article 94(3) EPC dated Jul. 17, 2018.
McLachlan et al., "Directed Enzyme Evolution and High-Throughput Screening", Biocatalysis for the Pharmaceutical Industry: Discovery, Development, and Manufacturing, pp. 45-64, (2009), Retrieved from the Internet: URL:http://www.scs.illinois.edu/~zhaogrp/publications/HZ72.pdf [retrieved on Jul. 11, 2018].

*Primary Examiner* — Tekchand Saidha
(74) *Attorney, Agent, or Firm* — Michele M. Wales; Inhouse Patent Counsel, LLC

(57) ABSTRACT

Described are alkenol dehydratase variants having improved activity in catalyzing the conversion of prenol into isoprene, methods for the production of isoprene using such enzyme variants and their uses in the production of isoprene from prenol.

12 Claims, 1 Drawing Sheet
Specification includes a Sequence Listing.

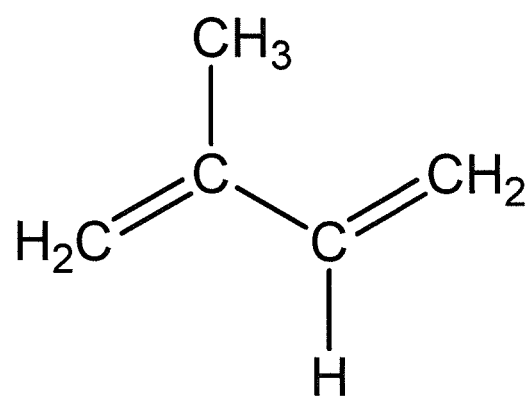

ALKENOL DEHYDRATASE VARIANTS

CROSS-REFERENCE TO RELATED APPLICATIONS

This application is a § 371 National Stage Application of PCT/EP2015/076450 filed on Nov. 12, 2015, which claims priority to EP 14193010.7 filed on Nov. 13, 2014. Both of these documents are hereby incorporated by reference in their entirety.

The present invention relates to alkenol dehydratase variants having improved activity in catalyzing the conversion of prenol (3-methylbut-3-en-2-ol) into isoprene.

Isoprene (2-methyl-1,3-butadiene; see FIG. 1) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes. The C5 skeleton can also be synthesised from smaller subunits. Due to the desire to be able to produce isoprene in methods which are independent from non-renewable resources, attempts have been made to provide methods for producing isoprene enzymatically making use of genetically modified microorganisms. In nature isoprenes, a large and diverse class of organic molecules derived from five-carbon isoprene units is found in all living kingdom. The two major isoprenoid precursors, isopentenyl pyrophosphate and dimethylallyl pyrophosphate, occur by two distinct metabolic pathways (Julsing et al.; Appl. Microbiol. Technol. 75 (2007), 1377-1384). In eukaryotes and archae isoprenoid precursors are formed via the mevalonate (MVA) pathway, while some eubacteria and higher plants produce isoprene via the methylerythritol phosphate (MEP) pathway. Accordingly, there are some reports on the genetic modification of microorganisms exploiting these pathways. For example, WO2010/031062 describes the increase of isoprene production by using the archaeal lower mevalonate pathway. US 2011/0039323 A1 describes a method for producing isoprene by providing microorganisms that express certain enzymes of the MEP pathway. WO2010/031076 describes the conversion of prenyl derivatives into isoprene by making use of isoprene synthase. This includes the conversion of isoprenol diphosphate and prenol diphosphate into isoprene using an isoprene synthase.

Recent work has shown that it is possible to generate isoprene through an enzymatic process by converting prenol (3-methylbut-2-en-1-ol) into isoprene utilizing a dehydratase, in particular a linalool dehydratase-isomerase (WO 2014/033129).

However, the activity rate of the enzymes occurring in nature is not yet suitable for industrial applications and, hence, there is a need for improvements, i.e., to increase the activity of such enzymes, in particular as regards to a further increase in efficiency of the above processes so as to make them more suitable for industrial purposes.

The present invention addresses this need by providing the embodiments as defined in the claims.

Thus, the present invention provides an alkenol dehydratase variant which is characterized in that it is capable of converting prenol into isoprene with an improved activity over the activity of the alkenol dehydratase from which it is derived.

In particular, the present invention relates to a variant of an alkenol dehydratase variant showing an improved activity in converting prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 2, 7, 54, 55, 58, 88, 94, 105, 110, 111, 112, 113, 117, 139, 171, 177, 189, 203, 208, 231, 240, 257, 270, 291, 299, 305, 349, 350, 395 and 397 in the amino acid sequence shown in SEQ ID NO:1.

In the context of the present invention, an "improved activity" means that the activity of the enzyme in question is at least 10%, preferably at least 20%, more preferably at least 30% or 50%, even more preferably at least 70% or 80% and particularly preferred at least 90% or 100% higher than that of the enzyme from which the variant is derived, preferably higher than that of the alkenol dehydratase represented by SEQ ID NO:1. In even more preferred embodiments, the "improved activity" may be at least 150%, at least 200%, at least 300%, at least 750% or at least 1000% higher than that of the corresponding enzyme from which the variant is derived, preferably higher than that of the alkenol dehydratase represented by SEQ ID NO:1. In a particularly preferred embodiment, the activity is measured by using an assay with a purified enzyme and chemically synthesized prenol as described below. The improved activity of a variant can be measured as a higher isoprene production in a given time under defined conditions, compared with the parent enzyme. This improved activity can result from a higher turnover number, e.g., a higher kcat value. It can also result from a lower Km value. It can also result from a higher kcat/Km value. Finally, it can also result from a higher solubility or stability of the enzyme. The degree of improvement can be measured as the improvement in isoprene production. The degree of improvement can also be measured in terms of soluble protein production.

In accordance with the present invention, the provided enzyme variants which are capable of converting prenol into isoprene with a higher turnover number under the conditions described below show a turnover rate of at least $1\times10^{-1}$ s$^{-1}$, more preferably of 1 s$^{-1}$, even more preferably of 10 s$^{-1}$, or even more preferably of at least 1000 s$^{-1}$ of prenol into isoprene. The corresponding wild-type enzyme has a turnover rate of about $0.77\times10^{-1}$ s$^{-1}$ of prenol into isoprene.

The enzyme variants which the present invention provides are capable of converting prenol into isoprene with an activity which is at least 1.25 times as high compared to the turnover rate of the corresponding wild type enzyme having the amino acid sequence as shown in SEQ ID NO:1. In a more preferred embodiment, the enzyme variants which are capable of converting prenol into isoprene have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

Such enzyme variants are obtained by effecting mutations at specific positions in an alkenol dehydratase and the variants obtained by effecting such mutations show an improved activity in catalyzing the conversion of prenol into isoprene. The turnover rate of an enzyme capable of converting prenol into isoprene may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used.

More specifically, the enzyme whose turnover rate is to be assessed may be determined as outlined in the following: Michaelis-Menten $k_{cat}$ and $K_m$ steady state kinetic constants for the reaction of conversion of prenol into isoprene may be determined using the following protocol: The alkenol dehydratase variant to be tested is sub-cloned into the commercial pET300/NT-DEST expression vector (Life technologies), transformed into BL21(DE3) competent cells and plated out on LB agar plates supplemented with the appropriate antibiotic. Isolated transformants are used to inoculate auto-induction medium (Studier F. W, Protein Expr. Purif. 41 (2005), 207-234) and the cultures are incubated overnight at 30° C. in a shaker incubator. Cell pellets obtained from a 200 ml culture and containing the overexpressed recombinant enzyme are stored overnight at −80° C. before being resuspended in 3 ml of lysis buffer (50 mM Tris-Cl pH7.5, 4 mM DTT, 25 mM MgCl$_2$, 25 mM KCl, 20 mM glutathion) supplemented with 10 μl Merck Novagen Lysonase. The cell suspension is incubated for 10 minutes at room temperature followed by 20 minutes on ice. Cell lysates are clarified by centrifugation (10 000 rpm for 20 minutes) and the supernatant is concentrated 3-fold using a filtration concentrator (Millipore Amicon) to a final volume of 1 ml. 500 μl enzymatic reactions are set up in 2 ml glass vials with 200 μl of the concentrated cell lysate supernatant (variant), with 200 μl of the concentrated cell lysate supernatant (cell transformed with empty vector) and a range of 20, 40, 80, 120 mM prenol concentrations (Sigma Aldrich). The vials are sealed and incubated for 20, 40, 60, 90, 120 and 180 min at 37° C. The amount of enzyme variants is quantified on SDS-PAGE gel against a BSA calibration curve. The enzymatic reactions are stopped by incubation for 5 minutes at 80° C. and the isoprene produced is quantified by gas chromatography. For the GC headspace analysis, 100 μl of the headspace gas is injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:10 and the FID detector temperature at 250° C. Nitrogen is used as a carrier gas (constant flow of 1.5 ml/min) and a mixture of air (air flow 300 ml/min), nitrogen (25 ml/min flow) and hydrogen (flow of 30 ml/min) is used to supply the FID detection system. Using these parameters, isoprene has a retention time of 5.75 min. The production rates of isoprene (mole of isoprene/mole enzyme/sec) are plotted as a function of the concentration of prenol and the curve is fitted using the Michaelis Menten equation ($V=(V_{max}*(substrate))/(K_m+(substrate))$) to extract the $k_{cat}$ (s$^{-1}$) and the $K_m$ values (mM).

By providing the above described enzyme variant, the present invention allows to dramatically increase the production efficiency of isoprene from prenol.

The term "alkenol dehydratase" refers to an enzyme which can dehydrate an alkenol, preferably, it is an enzyme which can dehydrate at least one compound corresponding to the general formula $C_nH_{2n}O$, with 3<n<7, and wherein the product of the reaction is $C_nH_{2n-2}+H_2O$. This activity can be measured in assays as described herein further below and in the appended Examples. In a preferred embodiment the alkenol dehydratase is a prenol dehydratase. The term "prenol dehydratase" in the context of the present invention refers to an enzyme which is capable converting prenol into isoprene. This activity can be measured by assays as described further below and in particular in the Example section. It could be shown that enzymes classified as linalool dehydratase-isomerase (EC 4.2.1.127) are suitable prenol dehydratases and are able to catalyze the conversion of prenol into isoprene. A linalool dehydratase-isomerase is an enzyme which has the ability to convert geraniol to linalool via an isomerisation and the ability to convert linalool to myrcene via a dehydration reaction. Thus, in a preferred embodiment the term "alkenol dehydratase" when used in the context of the present invention refers to a linalool dehydratase-isomerase. In another preferred embodiment, the term "alkenol dehydratase" refers to an enzyme which is derived from a linalool dehydratase-isomerase and which has the ability to convert prenol into isoprene. The enzyme designated linalool dehydratase-isomerase has been identified in *Castellaniella defragrans* (formerly *Alcaligenes defragrans*) strain 65Phen (Brodkorb et al., J. Biol. Chem. 285 (2010), 30436-30442). Linalool dehydratase-isomerase is a bifunctional enzyme which is involved in the anaerobic degradation of monoterpenes. The native enzyme has been found to have a molecular mass of 160 kDa and is assumed to be a homotetramer of 40 kDa subunits. The enzyme catalyzes in vitro two reactions in both directions depending on the thermodynamic driving forces. On the one hand, the enzyme catalyzes the isomerisation of the primary allylalcohol geraniol into its stereoisomer linalool which bears a tertiary allyl alcohol motif. On the other hand, the enzyme catalyzes the water secession (dehydration) from the tertiary alcohol linalool to the corresponding acyclic monoterpene beta-myrcene, a molecule bearing a conjugated diene motif. In *Castellaniella defragrans* the protein is expressed as a precursor protein with a signal peptide for a periplasmatic location which is cleaved after transport through the membrane. The enzyme is classified as EC 4.2.1.127. A linalool dehydratase-isomerase has the capacity to catalyze the following reaction under anaerobic conditions:

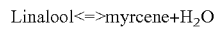

Linalool<=>myrcene+H$_2$O

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with CO$_2$/N$_2$ (10/90 (v/v)). The reaction is started by adding a distinct concentration of linalool and incubated at 35° C. The conversion of linalool into myrcene is assessed by investigating the production of myrcene, e.g. by gas chromatography.

In a preferred embodiment, a linalool dehydratase-isomerase also has the capacity to catalyze the isomerisation of geraniol into linalool under anaerobic conditions:

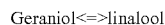

Geraniol<=>linalool

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with CO$_2$/N$_2$ (10/90 (v/v)). The reaction is started by adding a distinct concentration of geraniol and incubated at 35° C. The conversion of geraniol into linalool is assessed by investigating the production of myrcene, i.e. the product of the second reaction catalyzed by the enzyme, e.g. by gas chromatography.

Geraniol, linalool and myrcene are acyclic C$_{10}$-terpenoids produced by plants, belonging to the class of allylalcohols and hydrocarbons, respectively. Lüddecke and Harder (Z.

Naturforsch. 66c (2011), 409-412) reported on a high substrate specificity of linalool dehydratase-isomerase.

As mentioned above, it had been found that linalool dehydratase-isomerase can act on prenol converting it into isoprene. The present invention provides now improved variants of enzymes which are capable of converting prenol into isoprene. The inventors used as a model enzyme the linalool dehydratase-isomerase of *Castellaniella defragrans* shown in SEQ ID NO: 1 and could show that it is possible to provide variants of this enzyme which show increased activity with respect to the conversion of prenol into isoprene.

The model enzyme, i.e., the linalool dehydratase-isomerase of *Castellaniella defragrans*, as used by the inventors has the following amino acid sequence:

```
                                              (SEQ ID NO: 1)
MRFTLKTTAIVSAAALLAGFGPPPRAAELPPGRLATTEDYFAQQAKQAVT

PDVMAQLAYMNYIDFISPFYSRGCSFEAWELKHTPQRVIKYSIAFYAYGL

ASVALIDPKLRALAGHDLDIAVSKMKCKRVWGDWEEDGFGTDPIEKENIM

YKGHLNLMYGLYQLVTGSRRYEAEHAHLTRIIHDEIAANPFAGIVCEPDN

YFVQCNSVAYLSLWVYDRLHGTDYRAATRAWLDFIQKDLIDPERGAFYLS

YHPESGAVKPWISAYTTWTLAMVHGMDPAFSERYYPRFKQTFVEVYDEGR

KARVRETAGTDDADGGVGLASAFTLLLAREMGDQQLFDQLLNHLEPPAKP

SIVSASLRYEHPGSLLFDELLFLAKVHAGFGALLRMPPPAAKLAGK.
```

In one preferred embodiment the variants of the present invention are characterized by the feature that they are derived from an alkenol dehydratase, more preferably a linalool dehydratase-isomerase, having the amino acid sequence shown in SEQ ID NO:1 or a highly related sequence (at least 60% identical) and in which mutations are effected at one or more of the indicated positions and by the feature that they show the ability to convert prenol into isoprene and that they can do this with an improved activity. In a preferred embodiment the variant according to the present invention is derived from a sequence which shows at least 80% sequence identity to SEQ ID NO:1 and in which one or more substitutions and/or deletions and/or insertions at the positions indicated herein have been effected.

However, the teaching of the present invention is not restricted to the linalool dehydratase-isomerase enzyme of *Castellaniella defragrans* shown in SEQ ID NO: 1 which had been used as a model enzyme but can be extended to alkenol dehydratases from other organisms, in particular to other linalool dehydratase-isomerases, or to enzymes which are structurally related to SEQ ID NO:1 such as, e.g., truncated variants of the enzyme. Thus, the present invention also relates to variants of alkenol dehydratases, in particular to other linalool dehydratase-isomerases, which are structurally related to the *Castellaniella defragrans* sequence (SEQ ID NO: 1) and which show one or more substitutions and/or deletions and/or insertions at positions corresponding to any of the positions as indicated herein. The term "structurally related" refers to alkenol dehydratases, in particular to linalool dehydratase-isomerases, which show a sequence identity of at least n % to the sequence shown in SEQ ID NO: 1 with n being an integer between 60 and 100, preferably 60, 65, 70, 75, 80, 85, 90, 91, 92, 93, 94, 95, 96, 97, 98 or 99. In a preferred embodiment the structurally related alkenol dehydratases is of prokaryotic origin, even more preferably it stems from a bacterium, most preferably of a bacterium of the genus *Castellaniella*.

Thus, in one embodiment the variant of an alkenol dehydratase, in particular of a linalool dehydratase-isomerase, according to the present invention has or preferably is derived from a sequence which is at least n % identical to SEQ ID NO:1 with n being an integer between 60 and 100, preferably 60, 65, 70, 75, 80, 85, 90, 91, 92, 93, 94, 95, 96, 97, 98 or 99, and it has (a) substitution(s) and/or (a) deletion and/or (an) insertion(s) at a position as indicated herein. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap. Preferably, the degree of identity is calculated over the complete length of the sequence.

Amino acid residues located at a position corresponding to a position as indicated herein in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above or below indicated positions of SEQ ID NO:1. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of alkenol dehydratases are aligned by means of such a method, regardless of insertions or deletions that occur in the amino acid sequences, the positions of the corresponding amino acid residues can be determined in each of the alkenol dehydratases.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

The present invention relates in a preferred embodiment to a variant of an alkenol dehydratase showing an improved activity in converting prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 2, 7, 54, 55, 58, 88, 94, 105, 110, 111, 112, 113, 117, 139, 171, 177, 189, 203, 208, 231, 240, 257, 270, 291, 299, 305, 349, 350, 395 and 397 in the amino acid sequence shown in SEQ ID NO:1.

In a preferred embodiment such an alkenol dehydratase variant has an amino acid sequence as shown in SEQ ID NO:1 or an amino acid sequence having at least 60% sequence identity to SEQ ID NO:1, in which one or more amino acid residues at a position selected from the group consisting of positions 2, 7, 54, 55, 58, 88, 94, 105, 110, 111, 112, 113, 117, 139, 171, 177, 189, 203, 208, 231, 240, 257, 270, 291, 299, 305, 349, 350, 395 and 397 in the amino acid sequence shown in SEQ ID NO:1 or at a position corresponding to any of these positions, are substituted with another amino acid residue or deleted or wherein an insertion has been effected at one or more of these positions and said alkenol dehydratase has an improved activity in converting prenol into isoprene.

According to one embodiment, such an alkenol dehydratase variant has an amino acid sequence as shown in SEQ ID NO:1 in which (1) an amino acid residue at position 2 in the amino acid sequence shown in SEQ ID NO:1 or at a position corresponding to this position, is deleted or substituted with cysteine; and/or (2) an amino acid residue at position 7 in the amino acid sequence shown in SEQ ID NO:1 or at a position corresponding to this position, is deleted or substituted with valine; and/or (3) an amino acid residue at position 54 in the amino acid sequence shown in SEQ ID NO:1 or at a position corresponding to this position, is deleted or substituted with alanine or histidine; and/or (4) an amino acid residue at position 55 in the amino acid sequence shown in SEQ ID NO:1 or at a position corresponding to this position, is deleted or substituted with tyrosine; and/or (5) an amino acid residue at position 58 in the amino acid sequence shown in SEQ ID NO:1 or at a position corresponding to this position, is deleted or substituted with serine or threonine; and/or (6) an amino acid residue at position 88 in the amino acid sequence shown in SEQ ID NO:1 or at a position corresponding to this position, is deleted or substituted with threonine; and/or (7) an amino acid residue at position 94 in the amino acid sequence shown in SEQ ID NO:1 or at a position corresponding to this position, is deleted or substituted with glycine; and/or (8) an amino acid residue at position 105 in the amino acid sequence shown in SEQ ID NO:1 or at a position corresponding to this position, is deleted or substituted with alanine, glutamine or asparagine; and/or (9) an amino acid residue at position 110 in the amino acid sequence shown in SEQ ID NO:1 or at a position corresponding to this position, is deleted or substituted with valine; and/or

(10) an amino acid residue at position 111 in the amino acid sequence shown in SEQ ID NO:1 or at a position corresponding to this position, is deleted or substituted with glycine, leucine, isoleucine, asparagine, serine, threonine, or valine; and/or

(11) an amino acid residue at position 112 in the amino acid sequence shown in SEQ ID NO:1 or at a position corresponding to this position, is deleted or substituted with glycine, isoleucine, leucine, asparagine, threonine or valine; and/or

(12) an amino acid residue at position 113 in the amino acid sequence shown in SEQ ID NO:1 or at a position corresponding to this position, is deleted or substituted with threonine; and/or

(13) an amino acid residue at position 117 in the amino acid sequence shown in SEQ ID NO:1 or at a position corresponding to this position, is deleted or substituted with asparagine; and/or

(14) an amino acid residue at position 139 in the amino acid sequence shown in SEQ ID NO:1 or at a position corresponding to this position, is deleted or substituted with tyrosine; and/or

(15) an amino acid residue at position 171 in the amino acid sequence shown in SEQ ID NO:1 or at a position corresponding to this position, is deleted or substituted with phenylalanine; and/or
(16) an amino acid residue at position 177 in the amino acid sequence shown in SEQ ID NO:1 or at a position corresponding to this position, is deleted or substituted with glycine; and/or
(17) an amino acid residue at position 189 in the amino acid sequence shown in SEQ ID NO:1 or at a position corresponding to this position, is deleted or substituted with histidine; and/or
(18) an amino acid residue at position 203 in the amino acid sequence shown in SEQ ID NO:1 or at a position corresponding to this position, is deleted or substituted with isoleucine or threonine; and/or
(19) an amino acid residue at position 208 in the amino acid sequence shown in SEQ ID NO:1 or at a position corresponding to this position, is deleted or substituted with proline; and/or
(20) an amino acid residue at position 231 in the amino acid sequence shown in SEQ ID NO:1 or at a position corresponding to this position, is deleted or substituted with tyrosine; and/or
(21) an amino acid residue at position 240 in the amino acid sequence shown in SEQ ID NO:1 or at a position corresponding to this position, is deleted or substituted with glycine, leucine, glutamine, arginine, threonine, tryptophan or tyrosine; and/or
(22) an amino acid residue at position 257 in the amino acid sequence shown in SEQ ID NO:1 or at a position corresponding to this position, is deleted or substituted with leucine or valine; and/or
(23) an amino acid residue at position 270 in the amino acid sequence shown in SEQ ID NO:1 or at a position corresponding to this position, is deleted or substituted with leucine; and/or
(24) an amino acid residue at position 291 in the amino acid sequence shown in SEQ ID NO:1 or at a position corresponding to this position, is deleted or substituted with tryptophan or glutamic acid; and/or
(25) an amino acid residue at position 299 in the amino acid sequence shown in SEQ ID NO:1 or at a position corresponding to this position, is deleted or substituted with aspartic acid; and/or
(26) an amino acid residue at position 305 in the amino acid sequence shown in SEQ ID NO:1 or at a position corresponding to this position, is deleted or substituted with leucine; and/or
(27) an amino acid residue at position 349 in the amino acid sequence shown in SEQ ID NO:1 or at a position corresponding to this position, is deleted or substituted with serine; and/or
(28) an amino acid residue at position 350 in the amino acid sequence shown in SEQ ID NO:1 or at a position corresponding to this position, is deleted or substituted with glycine, glutamine or leucine; and/or
(29) an amino acid residue at position 395 in the amino acid sequence shown in SEQ ID NO:1 or at a position corresponding to this position, is deleted or substituted with aspartic acid or serine; and/or
(30) an amino acid residue at position 397 in the amino acid sequence shown in SEQ ID NO:1 or at a position corresponding to this position, is deleted or substituted with glutamine.

The present invention also relates to an alkenol dehydratase variant as described herein above which furthermore shows at least one modification at positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

According to one embodiment, such an alkenol dehydratase variant as described herein above which furthermore shows at least one modification at positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1 is an alkenol dehydratase variant, wherein
(1) an amino acid residue at position 195 in the amino acid sequence shown in SEQ ID NO:1 or at a position corresponding to this position, is deleted or substituted with phenylalanine or tyrosine; and/or
(2) an amino acid residue at position 132 in the amino acid sequence shown in SEQ ID NO:1 or at a position corresponding to this position, is deleted or substituted with alanine, lysine, arginine, glutamine, methionine, serine, valine, aspartic acid, asparagine, threonine, or glycine; and/or
(3) an amino acid residue at position 84 in the amino acid sequence shown in SEQ ID NO:1 or at a position corresponding to this position, is deleted or substituted with histidine or isoleucine; and/or
(4) an amino acid residue at position 18 in the amino acid sequence shown in SEQ ID NO:1 or at a position corresponding to this position, is deleted or substituted with valine, isoleucine or cysteine; and/or
(5) an amino acid residue at position 73 in the amino acid sequence shown in SEQ ID NO:1 or at a position corresponding to this position, is deleted or substituted with serine or alanine; and/or
(6) an amino acid residue at position 77 in the amino acid sequence shown in SEQ ID NO:1 or at a position corresponding to this position, is deleted or substituted with isoleucine or leucine; and/or
(7) an amino acid residue at position 386 in the amino acid sequence shown in SEQ ID NO:1 or at a position corresponding to this position, is deleted or substituted with serine; and/or
(8) an amino acid residue at position 119 in the amino acid sequence shown in SEQ ID NO:1 or at a position corresponding to this position, is deleted or substituted with histidine, glutamine, arginine or glycine; and/or
(9) an amino acid residue at position 251 in the amino acid sequence shown in SEQ ID NO:1 or at a position corresponding to this position, is deleted or substituted with methionine or asparagine; and/or
(10) an amino acid residue at position 141 in the amino acid sequence shown in SEQ ID NO:1 or at a position corresponding to this position, is deleted or substituted with serine; and/or
(11) an amino acid residue at position 123 in the amino acid sequence shown in SEQ ID NO:1 or at a position corresponding to this position, is deleted or substituted with glutamic acid, aspartic acid, tryptophan or arginine; and/or

(12) an amino acid residue at position 364 in the amino acid sequence shown in SEQ ID NO:1 or at a position corresponding to this position, is deleted or substituted with serine; and/or
(13) an amino acid residue at position 151 in the amino acid sequence shown in SEQ ID NO:1 or at a position corresponding to this position, is deleted or substituted with phenylalanine or methionine; and/or
(14) an amino acid residue at position 312 in the amino acid sequence shown in SEQ ID NO:1 or at a position corresponding to this position, is deleted or substituted with glutamic acid; and/or
(15) an amino acid residue at position 318 in the amino acid sequence shown in SEQ ID NO:1 or at a position corresponding to this position, is deleted or substituted with alanine or glycine; and/or
(16) an amino acid residue at position 168 in the amino acid sequence shown in SEQ ID NO:1 or at a position corresponding to this position, is deleted or substituted with aspartic acid; and/or
(17) an amino acid residue at position 19 in the amino acid sequence shown in SEQ ID NO:1 or at a position corresponding to this position, is deleted or substituted with threonine; and/or
(18) an amino acid residue at position 8 in the amino acid sequence shown in SEQ ID NO:1 or at a position corresponding to this position, is deleted or substituted with leucine; and/or
(19) an amino acid residue at position 195 in the amino acid sequence shown in SEQ ID NO:1 or at a position corresponding to this position, is deleted or substituted with leucine; and/or
(20) an amino acid residue at position 39 in the amino acid sequence shown in SEQ ID NO:1 or at a position corresponding to this position, is deleted or substituted with alanine; and/or
(21) an amino acid residue at position 170 in the amino acid sequence shown in SEQ ID NO:1 or at a position corresponding to this position, is deleted or substituted with lysine; and/or
(22) an amino acid residue at position 181 in the amino acid sequence shown in SEQ ID NO:1 or at a position corresponding to this position, is deleted or substituted with leucine or serine; and/or
(23) an amino acid residue at position 199 in the amino acid sequence shown in SEQ ID NO:1 or at a position corresponding to this position, is deleted or substituted with asparagine, alanine, glutamic acid, leucine, methionine, glutamine or serine; and/or
(24) an amino acid residue at position 269 in the amino acid sequence shown in SEQ ID NO:1 or at a position corresponding to this position, is deleted or substituted with alanine; and/or
(25) an amino acid residue at position 367 in the amino acid sequence shown in SEQ ID NO:1 or at a position corresponding to this position, is deleted or substituted with phenylalanine; and/or
(26) an amino acid residue at position 324 in the amino acid sequence shown in SEQ ID NO:1 or at a position corresponding to this position, is deleted or substituted with serine; and/or
(27) an amino acid residue at position 13 in the amino acid sequence shown in SEQ ID NO:1 or at a position corresponding to this position, is deleted or substituted with leucine or isoleucine; and/or
(28) an amino acid residue at position 173 in the amino acid sequence shown in SEQ ID NO:1 or at a position corresponding to this position, is deleted or substituted with arginine; and/or
(29) an amino acid residue at position 389 in the amino acid sequence shown in SEQ ID NO:1 or at a position corresponding to this position, is deleted or substituted with leucine; and/or
(30) an amino acid residue at position 118 in the amino acid sequence shown in SEQ ID NO:1 or at a position corresponding to this position, is deleted or substituted with leucine; and/or
(31) an amino acid residue at position 144 in the amino acid sequence shown in SEQ ID NO:1 or at a position corresponding to this position, is deleted or substituted with threonine; and/or
(32) an amino acid residue at position 12 in the amino acid sequence shown in SEQ ID NO:1 or at a position corresponding to this position, is deleted or substituted with alanine; and/or
(33) an amino acid residue at position 382 in the amino acid sequence shown in SEQ ID NO:1 or at a position corresponding to this position, is deleted or substituted with glutamine or aspartic acid; and/or
(34) an amino acid residue at position 145 in the amino acid sequence shown in SEQ ID NO:1 or at a position corresponding to this position, is deleted or substituted with proline or glutamic acid; and/or
(35) an amino acid residue at position 20 in the amino acid sequence shown in SEQ ID NO:1 or at a position corresponding to this position, is deleted or substituted with threonine or leucine; and/or
(36) an amino acid residue at position 122 in the amino acid sequence shown in SEQ ID NO:1 or at a position corresponding to this position, is deleted or substituted with methionine or leucine; and/or
(37) an amino acid residue at position 71 in the amino acid sequence shown in SEQ ID NO:1 or at a position corresponding to this position, is deleted or substituted with alanine, aspartic acid, or threonine; and/or
(38) an amino acid residue at position 72 in the amino acid sequence shown in SEQ ID NO:1 or at a position corresponding to this position, is deleted or substituted with leucine, proline, or arginine; and/or
(39) an amino acid residue at position 75 in the amino acid sequence shown in SEQ ID NO:1 or at a position corresponding to this position, is deleted or substituted with alanine, aspartic acid, phenylalanine, isoleucine, leucine, methionine, threonine, valine, or asparagine; and/or
(40) an amino acid residue at position 76 in the amino acid sequence shown in SEQ ID NO:1 or at a position corresponding to this position, is deleted or substituted with isoleucine, leucine or valine; and/or
(41) an amino acid residue at position 78 in the amino acid sequence shown in SEQ ID NO:1 or at a position corresponding to this position, is deleted or substituted with glycine; and/or
(42) an amino acid residue at position 79 in the amino acid sequence shown in SEQ ID NO:1 or at a position corresponding to this position, is deleted or substituted with tyrosine; and/or
(43) an amino acid residue at position 70 in the amino acid sequence shown in SEQ ID NO:1 or at a position corresponding to this position, is deleted or substituted with phenylalanine; and/or

(44) an amino acid residue at position 83 in the amino acid sequence shown in SEQ ID NO:1 or at a position corresponding to this position, is deleted or substituted with methionine, tryptophan, threonine; and/or
(45) an amino acid residue at position 115 in the amino acid sequence shown in SEQ ID NO:1 or at a position corresponding to this position, is deleted or substituted with alanine or aspartic acid; and/or
(46) an amino acid residue at position 116 in the amino acid sequence shown in SEQ ID NO:1 or at a position corresponding to this position, is deleted or substituted with lysine or arginine; and/or
(47) an amino acid residue at position 120 in the amino acid sequence shown in SEQ ID NO:1 or at a position corresponding to this position, is deleted or substituted with arginine or valine; and/or
(48) an amino acid residue at position 124 in the amino acid sequence shown in SEQ ID NO:1 or at a position corresponding to this position, is deleted or substituted with leucine; and/or
(49) an amino acid residue at position 126 in the amino acid sequence shown in SEQ ID NO:1 or at a position corresponding to this position, is deleted or substituted with alanine, aspartic acid or phenylalanine; and/or
(50) an amino acid residue at position 128 in the amino acid sequence shown in SEQ ID NO:1 or at a position corresponding to this position, is deleted or substituted with aspartic acid or asparagine; and/or
(51) an amino acid residue at position 129 in the amino acid sequence shown in SEQ ID NO:1 or at a position corresponding to this position, is deleted or substituted with leucine; and/or
(52) an amino acid residue at position 130 in the amino acid sequence shown in SEQ ID NO:1 or at a position corresponding to this position, is deleted or substituted with isoleucine; and/or
(53) an amino acid residue at position 131 in the amino acid sequence shown in SEQ ID NO:1 or at a position corresponding to this position, is deleted or substituted with phenylalanine; and/or
(54) an amino acid residue at position 135 in the amino acid sequence shown in SEQ ID NO:1 or at a position corresponding to this position, is deleted or substituted with proline; and/or
(55) an amino acid residue at position 138 in the amino acid sequence shown in SEQ ID NO:1 or at a position corresponding to this position, is deleted or substituted with glutamine; and/or
(56) an amino acid residue at position 143 in the amino acid sequence shown in SEQ ID NO:1 or at a position corresponding to this position, is deleted or substituted with tyrosine; and/or
(57) an amino acid residue at position 148 in the amino acid sequence shown in SEQ ID NO:1 or at a position corresponding to this position, is deleted or substituted with aspartic acid; and/or
(58) an amino acid residue at position 152 in the amino acid sequence shown in SEQ ID NO:1 or at a position corresponding to this position, is deleted or substituted with arginine; and/or
(59) an amino acid residue at position 155 in the amino acid sequence shown in SEQ ID NO:1 or at a position corresponding to this position, is deleted or substituted with isoleucine; and/or
(60) an amino acid residue at position 192 in the amino acid sequence shown in SEQ ID NO:1 or at a position corresponding to this position, is deleted or substituted with leucine; and/or
(61) an amino acid residue at position 193 in the amino acid sequence shown in SEQ ID NO:1 or at a position corresponding to this position, is deleted or substituted with alanine; and/or
(62) an amino acid residue at position 239 in the amino acid sequence shown in SEQ ID NO:1 or at a position corresponding to this position, is deleted or substituted with methionine; and/or
(63) an amino acid residue at position 252 in the amino acid sequence shown in SEQ ID NO:1 or at a position corresponding to this position, is deleted or substituted with aspartic acid; and/or
(64) an amino acid residue at position 253 in the amino acid sequence shown in SEQ ID NO:1 or at a position corresponding to this position, is deleted or substituted with histidine; and/or
(65) an amino acid residue at position 254 in the amino acid sequence shown in SEQ ID NO:1 or at a position corresponding to this position, is deleted or substituted with glycine, histidine or proline; and/or
(66) an amino acid residue at position 255 in the amino acid sequence shown in SEQ ID NO:1 or at a position corresponding to this position, is deleted or substituted with glycine, histidine, leucine, glutamine or tyrosine; and/or
(67) an amino acid residue at position 314 in the amino acid sequence shown in SEQ ID NO:1 or at a position corresponding to this position, is deleted or substituted with threonine; and/or
(68) an amino acid residue at position 319 in the amino acid sequence shown in SEQ ID NO:1 or at a position corresponding to this position, is deleted or substituted with arginine; and/or
(69) an amino acid residue at position 361 in the amino acid sequence shown in SEQ ID NO:1 or at a position corresponding to this position, is deleted or substituted with threonine; and/or
(70) an amino acid residue at position 366 in the amino acid sequence shown in SEQ ID NO:1 or at a position corresponding to this position, is deleted or substituted with valine; and/or
(71) an amino acid residue at position 383 in the amino acid sequence shown in SEQ ID NO:1 or at a position corresponding to this position, is deleted or substituted with tyrosine; and/or
(72) an amino acid residue at position 384 in the amino acid sequence shown in SEQ ID NO:1 or at a position corresponding to this position, is deleted or substituted with methionine or tyrosine; and/or
(73) an amino acid residue at position 387 in the amino acid sequence shown in SEQ ID NO:1 or at a position corresponding to this position, is deleted or substituted with aspartic acid or asparagine; and/or
(74) an amino acid residue at position 390 in the amino acid sequence shown in SEQ ID NO:1 or at a position corresponding to this position, is deleted or substituted with aspartic acid; and/or
(75) an amino acid residue at position 247 in the amino acid sequence shown in SEQ ID NO:1 or at a position corresponding to this position, is deleted or substituted with valine.

The present invention also relates to an alkenol dehydratase variant as described herein above which furthermore shows at least one modification at positions 71, 72, 75, 76, 84, 98, 102, 116, 119, 131, 135, 138, 158, 159, 173, 175, 181, 199, 230, 247, 254, 255, 269, 318, 357, 364, 367 and 387 as described below.

The present invention relates in a preferred embodiment to a variant of an alkenol dehydratase variant showing an improved activity in converting prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 71, 72, 75, 76, 84, 98, 102, 116, 119, 131, 135, 138, 158, 159, 173, 175, 181, 199, 230, 247, 254, 255, 269, 318, 357, 364, 367 and 387 in the amino acid sequence shown in SEQ ID NO:1, wherein (1) an amino acid residue at position 71 in the amino acid sequence shown in SEQ ID NO:1 or at a position corresponding to this position, is deleted or substituted with glutamine, alanine or asparagine; and/or (2) an amino acid residue at position 72 in the amino acid sequence shown in SEQ ID NO:1 or at a position corresponding to this position, is deleted or substituted with lysine or proline; and/or (3) an amino acid residue at position 75 in the amino acid sequence shown in SEQ ID NO:1 or at a position corresponding to this position, is deleted or substituted with glutamic acid, alanine or methionine; and/or (4) an amino acid residue at position 76 in the amino acid sequence shown in SEQ ID NO:1 or at a position corresponding to this position, is deleted or substituted with methionine, valine or threonine; and/or (5) an amino acid residue at position 84 in the amino acid sequence shown in SEQ ID NO:1 or at a position corresponding to this position, is deleted or substituted with aspartic acid or glutamic acid; and/or (6) an amino acid residue at position 98 in the amino acid sequence shown in SEQ ID NO:1 or at a position corresponding to this position, is deleted or substituted with leucine or methionine; and/or (7) an amino acid residue at position 102 in the amino acid sequence shown in SEQ ID NO:1 or at a position corresponding to this position, is deleted or substituted with phenylalanine; and/or (8) an amino acid residue at position 116 in the amino acid sequence shown in SEQ ID NO:1 or at a position corresponding to this position, is deleted or substituted with alanine or tyrosine; and/or (9) an amino acid residue at position 119 in the amino acid sequence shown in SEQ ID NO:1 or at a position corresponding to this position, is deleted or substituted with arginine, histidine, serine, threonine, glutamine or asparagine; and/or

(10) an amino acid residue at position 131 in the amino acid sequence shown in SEQ ID NO:1 or at a position corresponding to this position, is deleted or substituted with tyrosine; and/or

(11) an amino acid residue at position 135 in the amino acid sequence shown in SEQ ID NO:1 or at a position corresponding to this position, is deleted or substituted with isoleucine, lysine, leucine, threonine or arginine; and/or

(12) an amino acid residue at position 138 in the amino acid sequence shown in SEQ ID NO:1 or at a position corresponding to this position, is deleted or substituted with alanine, aspartic acid, leucine, methionine, asparagine, or serine.

(13) an amino acid residue at position 158 in the amino acid sequence shown in SEQ ID NO:1 or at a position corresponding to this position, is deleted or substituted with leucine; and/or

(14) an amino acid residue at position 159 in the amino acid sequence shown in SEQ ID NO:1 or at a position corresponding to this position, is deleted or substituted with leucine; and/or

(15) an amino acid residue at position 173 in the amino acid sequence shown in SEQ ID NO:1 or at a position corresponding to this position, is deleted or substituted with serine, threonine or valine; and/or

(16) an amino acid residue at position 175 in the amino acid sequence shown in SEQ ID NO:1 or at a position corresponding to this position, is deleted or substituted with methionine; and/or

(17) an amino acid residue at position 181 in the amino acid sequence shown in SEQ ID NO:1 or at a position corresponding to this position, is deleted or substituted with histidine, serine or leucine; and/or

(18) an amino acid residue at position 199 in the amino acid sequence shown in SEQ ID NO:1 or at a position corresponding to this position, is deleted or substituted with tryptophan or glutamic acid; and/or

(19) an amino acid residue at position 230 in the amino acid sequence shown in SEQ ID NO:1 or at a position corresponding to this position, is deleted or substituted with proline; and/or

(20) an amino acid residue at position 247 in the amino acid sequence shown in SEQ ID NO:1 or at a position corresponding to this position, is deleted or substituted with alanine or tryptophan; and/or

(21) an amino acid residue at position 254 in the amino acid sequence shown in SEQ ID NO:1 or at a position corresponding to this position, is deleted or substituted with asparagine or serine or glycine; and/or

(22) an amino acid residue at position 255 in the amino acid sequence shown in SEQ ID NO:1 or at a position corresponding to this position, is deleted or substituted with isoleucine; and/or

(23) an amino acid residue at position 269 in the amino acid sequence shown in SEQ ID NO:1 or at a position corresponding to this position, is deleted or substituted with cysteine, serine, threonine, alanine or valine; and/or

(24) an amino acid residue at position 318 in the amino acid sequence shown in SEQ ID NO:1 or at a position corresponding to this position, is deleted or substituted with alanine, cysteine or serine; and/or

(25) an amino acid residue at position 357 in the amino acid sequence shown in SEQ ID NO:1 or at a position corresponding to this position, is deleted or substituted with alanine, leucine or methionine; and/or

(26) an amino acid residue at position 364 in the amino acid sequence shown in SEQ ID NO:1 or at a position corresponding to this position, is deleted or substituted with methionine; and/or

(27) an amino acid residue at position 367 in the amino acid sequence shown in SEQ ID NO:1 or at a position corresponding to this position, is deleted or substituted with methionine or phenylalanine; and/or

(28) an amino acid residue at position 387 in the amino acid sequence shown in SEQ ID NO:1 or at a position corresponding to this position, is deleted or substituted with valine.

In a preferred embodiment such an alkenol dehydratase variant is a variant showing an improved activity in converting prenol into isoprene over the corresponding alkenol dehydratase from which it is derived, wherein the alkenol dehydratase variant has an amino acid sequence as shown in SEQ ID NO:1 or an amino acid sequence having at least 60% sequence identity to SEQ ID NO:1, in which one or more amino acid residues at a position selected from 71, 72, 75, 76, 84, 98, 102, 116, 119, 131, 135, 138, 158, 159, 173, 175, 181, 199, 230, 247, 254, 255, 269, 318, 357, 364, 367 and 387 in the amino acid sequence shown in SEQ ID NO:1 or at a position corresponding to any of these positions, are substituted with another amino acid residue or deleted or wherein an insertion has been effected at one or more of these positions and wherein said alkenol dehydratase has an improved activity in converting prenol into isoprene, wherein (1) an amino acid residue at position 71 in the amino acid sequence shown in SEQ ID NO:1 or at a position corresponding to this position, is deleted or substituted with glutamine, alanine or asparagine; and/or (2) an amino acid residue at position 72 in the amino acid sequence shown in SEQ ID NO:1 or at a position corresponding to this position, is deleted or substituted with lysine or proline; and/or (3) an amino acid residue at position 75 in the amino acid sequence shown in SEQ ID NO:1 or at a position corresponding to this position, is deleted or substituted with glutamic acid, alanine or methionine; and/or (4) an amino acid residue at position 76 in the amino acid sequence shown in SEQ ID NO:1 or at a position corresponding to this position, is deleted or substituted with methionine, valine or threonine; and/or (5) an amino acid residue at position 84 in the amino acid sequence shown in SEQ ID NO:1 or at a position corresponding to this position, is deleted or substituted with aspartic acid or glutamic acid; and/or (6) an amino acid residue at position 98 in the amino acid sequence shown in SEQ ID NO:1 or at a position corresponding to this position, is deleted or substituted with leucine or methionine; and/or (7) an amino acid residue at position 102 in the amino acid sequence shown in SEQ ID NO:1 or at a position corresponding to this position, is deleted or substituted with phenylalanine; and/or (8) an amino acid residue at position 116 in the amino acid sequence shown in SEQ ID NO:1 or at a position corresponding to this position, is deleted or substituted with alanine or tyrosine; and/or (9) an amino acid residue at position 119 in the amino acid sequence shown in SEQ ID NO:1 or at a position corresponding to this position, is deleted or substituted with arginine, histidine, serine, threonine, alanine, glutamine or asparagine; and/or

(10) an amino acid residue at position 131 in the amino acid sequence shown in SEQ ID NO:1 or at a position corresponding to this position, is deleted or substituted with asparagine, serine or tyrosine; and/or

(11) an amino acid residue at position 135 in the amino acid sequence shown in SEQ ID NO:1 or at a position corresponding to this position, is deleted or substituted with isoleucine, lysine, leucine, alanine, threonine or glutamine; and/or

(12) an amino acid residue at position 138 in the amino acid sequence shown in SEQ ID NO:1 or at a position corresponding to this position, is deleted or substituted with alanine, aspartic acid, leucine, methionine, asparagine, or serine.

(13) an amino acid residue at position 158 in the amino acid sequence shown in SEQ ID NO:1 or at a position corresponding to this position, is deleted or substituted with leucine; and/or

(14) an amino acid residue at position 159 in the amino acid sequence shown in SEQ ID NO:1 or at a position corresponding to this position, is deleted or substituted with leucine; and/or

(15) an amino acid residue at position 173 in the amino acid sequence shown in SEQ ID NO:1 or at a position corresponding to this position, is deleted or substituted with serine, threonine or valine; and/or

(16) an amino acid residue at position 175 in the amino acid sequence shown in SEQ ID NO:1 or at a position corresponding to this position, is deleted or substituted with methionine; and/or

(17) an amino acid residue at position 181 in the amino acid sequence shown in SEQ ID NO:1 or at a position corresponding to this position, is deleted or substituted with histidine, serine or leucine; and/or

(18) an amino acid residue at position 199 in the amino acid sequence shown in SEQ ID NO:1 or at a position corresponding to this position, is deleted or substituted with tryptophan or glutamic acid; and/or

(19) an amino acid residue at position 230 in the amino acid sequence shown in SEQ ID NO:1 or at a position corresponding to this position, is deleted or substituted with proline; and/or

(20) an amino acid residue at position 247 in the amino acid sequence shown in SEQ ID NO:1 or at a position corresponding to this position, is deleted or substituted with alanine or tryptophan; and/or

(21) an amino acid residue at position 254 in the amino acid sequence shown in SEQ ID NO:1 or at a position corresponding to this position, is deleted or substituted with asparagine, glycine or serine; and/or

(22) an amino acid residue at position 255 in the amino acid sequence shown in SEQ ID NO:1 or at a position corresponding to this position, is deleted or substituted with isoleucine; and/or

(23) an amino acid residue at position 269 in the amino acid sequence shown in SEQ ID NO:1 or at a position corresponding to this position, is deleted or substituted with cysteine, serine, threonine, alanine or valine; and/or

(24) an amino acid residue at position 318 in the amino acid sequence shown in SEQ ID NO:1 or at a position corresponding to this position, is deleted or substituted with alanine, cysteine or serine; and/or

(25) an amino acid residue at position 357 in the amino acid sequence shown in SEQ ID NO:1 or at a position corresponding to this position, is deleted or substituted with alanine, leucine or methionine; and/or

(26) an amino acid residue at position 364 in the amino acid sequence shown in SEQ ID NO:1 or at a position corresponding to this position, is deleted or substituted with methionine; and/or

(27) an amino acid residue at position 367 in the amino acid sequence shown in SEQ ID NO:1 or at a position corresponding to this position, is deleted or substituted with methionine or phenylalanine; and/or

(28) an amino acid residue at position 387 in the amino acid sequence shown in SEQ ID NO:1 or at a position corresponding to this position, is deleted or substituted with valine.

In a preferred embodiment, the variant according to the invention showing an improved activity in converting prenol into isoprene is characterized in that it contains at least two deletions, substitutions and/or insertions wherein the deletion/insertion/substitution is at position 112 in the amino acid sequence shown in SEQ ID NO:1 or at a position corresponding to this position and another deletion/insertion/substitution is at position 350 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 357, 364, 367, 387, 395 and 397.

Preferably, such a variant has the following substitutions in the amino acid sequence shown in SEQ ID NO:1 or at positions corresponding to these position: A112L-K350Q or A112V-K350L.

In a preferred embodiment, the variant according to the invention showing an improved activity in converting prenol into isoprene is characterized in that it contains at least two deletions, substitutions and/or insertions wherein the deletion/insertion/substitution is at position 173 in the amino acid sequence shown in SEQ ID NO:1 or at a position corresponding to this position and another deletion/insertion/substitution is at position 181 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 175, 177, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: A173S-I181L or A173T-I181L.

In a preferred embodiment, the variant according to the invention showing an improved activity in converting prenol into isoprene is characterized in that it contains at least two deletions, substitutions and/or insertions wherein the deletion/insertion/substitution is at position 173 in the amino acid sequence shown in SEQ ID NO:1 or at a position corresponding to this position and another deletion/insertion/substitution is at position 318 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 175, 177, 181, 199, 189, 203, 208, 230, 231, 240, 247, 254, 255, 257, 269, 270, 291, 299, 305, 349, 350, 395, 357, 364, 367, 387 and 397.

Preferably, such a variant has the following substitutions in the amino acid sequence shown in SEQ ID NO:1 or at positions corresponding to these position: A173V-V318A.

In a preferred embodiment, the variant according to the invention showing an improved activity in converting prenol into isoprene is characterized in that it contains at least two deletions, substitutions and/or insertions wherein the deletion/insertion/substitution is at position 119 in the amino acid sequence shown in SEQ ID NO:1 or at a position corresponding to this position and another deletion/insertion/substitution is at position 357 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 364, 367, 387 and 397.

Preferably, such a variant has the following substitutions in the amino acid sequence shown in SEQ ID NO:1 or at positions corresponding to these position: x D119H-S357A or D119R-S357M.

In a preferred embodiment, the variant according to the invention showing an improved activity in converting prenol into isoprene is characterized in that it contains at least two deletions, substitutions and/or insertions wherein the deletion/insertion/substitution is at position 135 in the amino acid sequence shown in SEQ ID NO:1 or at a position corresponding to this position and another deletion/insertion/substitution is at position 318 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 138, 139, 158, 159, 171, 173, 175, 177, 181, 199, 189, 203, 208, 230, 231, 240, 247, 254, 255, 257, 269, 270, 291, 299, 305, 349, 350, 395, 357, 364, 367, 387 and 397.

Preferably, such a variant has the following substitutions in the amino acid sequence shown in SEQ ID NO:1 or at positions corresponding to these position: E135I-V318A.

In a preferred embodiment, the variant according to the invention showing an improved activity in converting prenol into isoprene is characterized in that it contains at least two deletions, substitutions and/or insertions wherein the deletion/insertion/substitution is at position 76 in the amino acid sequence shown in SEQ ID NO:1 or at a position corresponding to this position and another deletion/insertion/substitution is at position 77 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: F76V-E77L.

In a preferred embodiment, the variant according to the invention showing an improved activity in converting prenol into isoprene is characterized in that it contains at least two deletions, substitutions and/or insertions wherein the deletion/insertion/substitution is at position 132 in the amino acid sequence shown in SEQ ID NO:1 or at a position corresponding to this position and another deletion/insertion/substitution is at position 318 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 349, 350, 395, 357, 364, 367, 387 and 397.

Preferably, such a variant has the following substitutions in the amino acid sequence shown in SEQ ID NO:1 or at positions corresponding to these position: G132S-V318S.

In a preferred embodiment, the variant according to the invention showing an improved activity in converting prenol into isoprene is characterized in that it contains at least two deletions, substitutions and/or insertions wherein the deletion/insertion/substitution is at position 116 in the amino acid sequence shown in SEQ ID NO:1 or at a position corresponding to this position and another deletion/insertion/substitution is at position 117 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: H116Y-D117N.

In a preferred embodiment, the variant according to the invention showing an improved activity in converting prenol into isoprene is characterized in that it contains at least two deletions, substitutions and/or insertions wherein the deletion/insertion/substitution is at position 126 in the amino acid sequence shown in SEQ ID NO:1 or at a position corresponding to this position and another deletion/insertion/substitution is at position 364 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 367, 387 and 397.

Preferably, such a variant has the following substitutions in the amino acid sequence shown in SEQ ID NO:1 or at positions corresponding to these position: K126F-G364M.

In a preferred embodiment, the variant according to the invention showing an improved activity in converting prenol into isoprene is characterized in that it contains at least two deletions, substitutions and/or insertions wherein the deletion/insertion/substitution is at position 105 in the amino acid sequence shown in SEQ ID NO:1 or at a position corresponding to this position and another deletion/insertion/substitution is at position 113 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 110, 111, 112, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: L105A-L113T or L105N-L113T.

In a preferred embodiment, the variant according to the invention showing an improved activity in converting prenol into isoprene is characterized in that it contains at least two deletions, substitutions and/or insertions wherein the deletion/insertion/substitution is at position 105 in the amino acid sequence shown in SEQ ID NO:1 or at a position corresponding to this position and another deletion/insertion/substitution is at position 112 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 110, 111, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: L105Q-A112T.

In a preferred embodiment, the variant according to the invention showing an improved activity in converting prenol into isoprene is characterized in that it contains at least two deletions, substitutions and/or insertions wherein the deletion/insertion/substitution is at position 110 in the amino acid sequence shown in SEQ ID NO:1 or at a position corresponding to this position and another deletion/insertion/substitution is at position 112 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 111, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: L110V-A112T.

In a preferred embodiment, the variant according to the invention showing an improved activity in converting prenol into isoprene is characterized in that it contains at least two deletions, substitutions and/or insertions wherein the deletion/insertion/substitution is at position 113 in the amino acid sequence shown in SEQ ID NO:1 or at a position corresponding to this position and another deletion/insertion/substitution is at position 177 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 116, 117, 119, 131, 135, 138, 139, 158, 159, 171, 173, 175, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: L113T-H177G.

In a preferred embodiment, the variant according to the invention showing an improved activity in converting prenol into isoprene is characterized in that it contains at least two deletions, substitutions and/or insertions wherein the deletion/insertion/substitution is at position 387 in the amino acid sequence shown in SEQ ID NO:1 or at a position corresponding to this position and another deletion/insertion/substitution is at position 395 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 357, 364, 367, 387 and 397.

Preferably, such a variant has the following substitutions in the amino acid sequence shown in SEQ ID NO:1 or at positions corresponding to these position: M387V-A395D or M387V-A395S.

In a preferred embodiment, the variant according to the invention showing an improved activity in converting prenol into isoprene is characterized in that it contains at least two deletions, substitutions and/or insertions wherein the deletion/insertion/substitution is at position 111 in the amino acid sequence shown in SEQ ID NO:1 or at a position corresponding to this position and another deletion/insertion/substitution is at position 349 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 350, 395, 357, 364, 367, 387 and 397.

Preferably, such a variant has the following substitutions in the amino acid sequence shown in SEQ ID NO:1 or at positions corresponding to these position: R111G-A349S.

In a preferred embodiment, the variant according to the invention showing an improved activity in converting prenol into isoprene is characterized in that it contains at least two deletions, substitutions and/or insertions wherein the deletion/insertion/substitution is at position 111 in the amino acid sequence shown in SEQ ID NO:1 or at a position corresponding to this position and another deletion/insertion/substitution is at position 119 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 112, 113, 116, 117, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: R111L-D119S.

In a preferred embodiment, the variant according to the invention showing an improved activity in converting prenol into isoprene is characterized in that it contains at least two deletions, substitutions and/or insertions wherein the deletion/insertion/substitution is at position 2 in the amino acid sequence shown in SEQ ID NO:1 or at a position corresponding to this position and another deletion/insertion/substitution is at position 240 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: R2C-I240E.

In a preferred embodiment, the variant according to the invention showing an improved activity in converting prenol into isoprene is characterized in that it contains at least two deletions, substitutions and/or insertions wherein the deletion/insertion/substitution is at position 75 in the amino acid sequence shown in SEQ ID NO:1 or at a position corresponding to this position and another deletion/insertion/substitution is at position 291 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 299, 305, 318, 349, 350, 395, 357, 364, 367, 387 and 397.

Preferably, such a variant has the following substitutions in the amino acid sequence shown in SEQ ID NO:1 or at positions corresponding to these position: S75M-Q291W.

In a preferred embodiment, the variant according to the invention showing an improved activity in converting prenol into isoprene is characterized in that it contains at least two deletions, substitutions and/or insertions wherein the deletion/insertion/substitution is at position 7 in the amino acid sequence shown in SEQ ID NO:1 or at a position corresponding to this position and another deletion/insertion/substitution is at position 181 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: T7V-I181S.

In a preferred embodiment, the variant according to the invention showing an improved activity in converting prenol into isoprene is characterized in that it contains at least two deletions, substitutions and/or insertions wherein the deletion/insertion/substitution is at position 88 in the amino acid sequence shown in SEQ ID NO:1 or at a position corresponding to this position and another deletion/insertion/substitution is at position 152 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: V88T-K152R.

In a preferred embodiment, the variant according to the invention showing an improved activity in converting prenol into isoprene is characterized in that it contains at least two deletions, substitutions and/or insertions wherein the deletion/insertion/substitution is at position 159 in the amino acid sequence shown in SEQ ID NO:1 or at a position corresponding to this position and another deletion/insertion/substitution is at position 397 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 171, 173, 175, 177, 181, 199, 189, 203, 208, 230, 231, 240, 247, 254, 255, 257, 269, 270, 291, 299, 305, 318, 349, 350, 395, 357, 364, 367, and 387.

Preferably, such a variant has the following substitutions in the amino acid sequence shown in SEQ ID NO:1 or at positions corresponding to these position: Y159L-K397Q.

In a preferred embodiment, the variant according to the invention showing an improved activity in converting prenol into isoprene is characterized in that it contains at least two deletions, substitutions and/or insertions wherein the deletion/insertion/substitution is at position 98 in the amino acid sequence shown in SEQ ID NO:1 or at a position corresponding to this position and another deletion/insertion/substitution is at position 299 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 305, 318, 349, 350, 395, 357, 364, 367, 387 and 397.

Preferably, such a variant has the following substitutions in the amino acid sequence shown in SEQ ID NO:1 or at positions corresponding to these position: Y98L-E299D.

In a preferred embodiment, the variant according to the invention showing an improved activity in converting prenol into isoprene is characterized in that it contains at least two deletions, substitutions and/or insertions wherein the deletion/insertion/substitution is at position 98 in the amino acid sequence shown in SEQ ID NO:1 or at a position corresponding to this position and another deletion/insertion/substitution is at position 291 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 299, 305, 318, 349, 350, 395, 357, 364, 367, 387 and 397.

Preferably, such a variant has the following substitutions in the amino acid sequence shown in SEQ ID NO:1 or at positions corresponding to these position: Y98M-Q291E.

In a preferred embodiment, the variant according to the invention showing an improved activity in converting prenol into isoprene is characterized in that it contains at least two deletions, substitutions and/or insertions wherein the deletion/insertion/substitution is at position 72 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: R72P-W269A.

In a preferred embodiment, the variant according to the invention showing an improved activity in converting prenol into isoprene is characterized in that it contains at least two deletions, substitutions and/or insertions wherein the deletion/insertion/substitution is at position 199 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 189, 203, 208, 230, 231, 240, 247, 254, 255, 257, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: D199E-W269A.

In a preferred embodiment, the variant according to the invention showing an improved activity in converting prenol into isoprene is characterized in that it contains at least two deletions, substitutions and/or insertions wherein the deletion/insertion/substitution is at position 71 in the amino acid sequence shown in SEQ ID NO:1 or at a position corresponding to this position and another deletion/insertion/substitution is at position 75 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 72, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: S71A-S75A.

In a preferred embodiment, the variant according to the invention showing an improved activity in converting prenol into isoprene is characterized in that it contains at least two deletions, substitutions and/or insertions wherein the deletion/insertion/substitution is at position 71 in the amino acid sequence shown in SEQ ID NO:1 or at a position corresponding to this position and another deletion/insertion/substitution is at position 135 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 72, 75, 76, 84, 88, 94, 98, 102, 105, 110, 111, 112, 113, 116, 117, 119, 131, 138, 139, 158, 159, 171, 173, 175, 177, 181, 199, 189, 203, 208, 230, 231, 240, 247, 254, 255, 257, 269, 270, 291, 299, 305, 318, 349, 350, 395, 357, 364, 367, 387 and 397.

Preferably, such a variant has the following substitutions in the amino acid sequence shown in SEQ ID NO:1 or at positions corresponding to these position: S71N-E135T.

In a preferred embodiment, the variant according to the invention showing an improved activity in converting prenol into isoprene is characterized in that it contains at least three deletions, substitutions and/or insertions wherein the deletion/insertion/substitution is at position 119 in the amino acid sequence shown in SEQ ID NO:1 or at a position corresponding to this position and another deletion/insertion/substitution is at position 350 in the amino acid sequence shown in SEQ ID NO:1 or at a position corresponding to this position and another deletion/insertion/substitution is at position 357 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 131, 135, 138, 139, 158, 159, 171, 173, 175, 177, 181, 199, 189, 203, 208, 230, 231, 240, 247, 254, 255, 257, 269, 270, 291, 299, 305, 318, 349, 395, 364, 367, 387 and 397.

Preferably, such a variant has the following substitutions in the amino acid sequence shown in SEQ ID NO:1 or at positions corresponding to these position: D119R-K350G-S357L.

In a preferred embodiment, the variant according to the invention showing an improved activity in converting prenol into isoprene is characterized in that it contains at least three deletions, substitutions and/or insertions wherein the deletion/insertion/substitution is at position 72 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: R72P-Y251M-W269A.

In a preferred embodiment, the variant according to the invention showing an improved activity in converting prenol into isoprene is characterized in that it contains at least three deletions, substitutions and/or insertions wherein the deletion/insertion/substitution is at position 112 in the amino acid sequence shown in SEQ ID NO:1 or at a position corresponding to this position and another deletion/insertion/substitution is at position 195 in the amino acid sequence shown in SEQ ID NO:1 or at a position corresponding to this position and another deletion/insertion/ substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: A112V-V195F-W269A.

In a preferred embodiment, the variant according to the invention showing an improved activity in converting prenol into isoprene is characterized in that it contains at least three deletions, substitutions and/or insertions wherein the deletion/insertion/substitution is at position 195 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: V195F-Y251M-W269A.

In a preferred embodiment, the variant according to the invention showing an improved activity in converting prenol into isoprene is characterized in that it contains at least three deletions, substitutions and/or insertions wherein the deletion/insertion/substitution is at position 195 in the amino acid sequence shown in SEQ ID NO:1 or at a position corresponding to this position and another deletion/insertion/substitution is at position 199 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 171, 173, 175, 177, 181, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: V195F-D199E-W269A.

In a preferred embodiment, the variant according to the invention showing an improved activity in converting prenol into isoprene is characterized in that it contains at least three deletions, substitutions and/or insertions wherein the deletion/insertion/substitution is at position 112 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: A112V-Y251M-W269A.

In a preferred embodiment, the variant according to the invention showing an improved activity in converting prenol into isoprene is characterized in that it contains at least three deletions, substitutions and/or insertions wherein the deletion/insertion/substitution is at position 75 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: S75A-Y251M-W269A.

In a preferred embodiment, the variant according to the invention showing an improved activity in converting prenol into isoprene is characterized in that it contains at least three deletions, substitutions and/or insertions wherein the deletion/insertion/substitution is at position 112 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: A112V-Y251N-W269A.

In a preferred embodiment, the variant according to the invention showing an improved activity in converting prenol into isoprene is characterized in that it contains at least three deletions, substitutions and/or insertions wherein the deletion/insertion/substitution is at position 112 in the amino acid sequence shown in SEQ ID NO:1 or at a position corresponding to this position and another deletion/insertion/substitution is at position 195 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: A112V-V195F-W269A.

In a preferred embodiment, the variant according to the invention showing an improved activity in converting prenol into isoprene is characterized in that it contains at least three deletions, substitutions and/or insertions wherein the deletion/insertion/substitution is at position 72 in the amino acid sequence shown in SEQ ID NO:1 or at a position corresponding to this position and another deletion/insertion/substitution is at position 75 in the amino acid sequence shown in SEQ ID NO:1 or at a position corresponding to this position and another deletion/insertion/substitution is at position 251 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: R72P-S75A-Y251M.

In a preferred embodiment, the variant according to the invention showing an improved activity in converting prenol into isoprene is characterized in that it contains at least three deletions, substitutions and/or insertions wherein the deletion/insertion/substitution is at position 75 in the amino acid sequence shown in SEQ ID NO:1 or at a position corresponding to this position and another deletion/insertion/substitution is at position 152 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: S75A-K152R-L367F.

In a preferred embodiment, the variant according to the invention showing an improved activity in converting prenol into isoprene is characterized in that it contains at least three deletions, substitutions and/or insertions wherein the deletion/insertion/substitution is at position 71 in the amino acid sequence shown in SEQ ID NO:1 or at a position corresponding to this position and another deletion/insertion/substitution is at position 119 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 72, 75, 76, 84, 88, 94, 98, 102, 105, 110, 111, 112, 113, 116, 117, 131, 135, 138, 139, 158, 159, 171, 173, 175, 177, 181, 199, 189, 203, 208, 230, 231, 240, 247, 254, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: S71A-D119Q-L367F.

In a preferred embodiment, the variant according to the invention showing an improved activity in converting prenol into isoprene is characterized in that it contains at least four deletions, substitutions and/or insertions wherein the deletion/insertion/substitution is at position 72 in the amino acid sequence shown in SEQ ID NO:1 or at a position corresponding to this position and another deletion/insertion/substitution is at position 195 in the amino acid sequence shown in SEQ ID NO:1 or at a position corresponding to this position and another deletion/insertion/substitution is at position 251 in the amino acid sequence shown in SEQ ID NO:1 or at a position corresponding to this position and another deletion/insertion/substitution is at position 269 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 75, 76, 84, 88, 94, 98, 102, 105, 110, 111, 112, 113, 116, 117, 119, 131, 135, 138, 139, 158, 159, 171, 173, 175, 177, 181, 199, 189, 203, 208, 230, 231, 240, 247, 254, 255, 257, 270, 291, 299, 305, 318, 349, 350, 357, 395, 364, 367, 387 and 397.

Preferably, such a variant has the following substitutions in the amino acid sequence shown in SEQ ID NO:1 or at positions corresponding to these position: R72P-V195F-Y251M-W269A.

In a preferred embodiment, the variant according to the invention showing an improved activity in converting prenol into isoprene is characterized in that it contains at least four deletions, substitutions and/or insertions wherein the deletion/insertion/substitution is at position 152 in the amino acid sequence shown in SEQ ID NO:1 or at a position corresponding to this position and another deletion/insertion/substitution is at position 171 in the amino acid sequence shown in SEQ ID NO:1 or at a position corresponding to this position and another deletion/insertion/substitution is at position 254 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 119, 131, 135, 138, 139, 158, 159, 173, 175, 177, 181, 199, 189, 203, 208, 230, 231, 240, 247, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: K152R-Y171F-E254G-L367F.

In a preferred embodiment, the variant according to the invention showing an improved activity in converting prenol into isoprene is characterized in that it contains at least four deletions, substitutions and/or insertions wherein the deletion/insertion/substitution is at position 75 in the amino acid sequence shown in SEQ ID NO:1 or at a position corresponding to this position and another deletion/insertion/substitution is at position 171 in the amino acid sequence shown in SEQ ID NO:1 or at a position corresponding to this position and another deletion/insertion/substitution is at position 199 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 76, 84, 88, 94, 98, 102, 105, 110, 111, 112, 113, 116, 117, 119, 131, 135, 138, 139, 158, 159, 173, 175, 177, 181, 189, 203, 208, 230, 231, 240, 247, 254, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: S75A-Y171F-D199E-L367F.

In a preferred embodiment, the variant according to the invention showing an improved activity in converting prenol into isoprene is characterized in that it contains at least four deletions, substitutions and/or insertions wherein the deletion/insertion/substitution is at position 119 in the amino acid sequence shown in SEQ ID NO:1 or at a position corresponding to this position and another deletion/insertion/substitution is at position 171 in the amino acid sequence shown in SEQ ID NO:1 or at a position corresponding to this position and another deletion/insertion/substitution is at position 254 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 112, 113, 116, 117, 131, 135, 138, 139, 158, 159, 173, 175, 177, 181, 199, 189, 203, 208, 230, 231, 240, 247, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: D119Q-Y171F-E254G-L367F.

In a preferred embodiment, the variant according to the invention showing an improved activity in converting prenol into isoprene is characterized in that it contains at least four deletions, substitutions and/or insertions wherein the deletion/insertion/substitution is at position 112 in the amino acid sequence shown in SEQ ID NO:1 or at a position corresponding to this position and another deletion/insertion/substitution is at position 152 in the amino acid sequence shown in SEQ ID NO:1 or at a position corresponding to this position and another deletion/insertion/substitution is at position 199 in the amino acid sequence shown in SEQ ID NO:1 or at a position corresponding to this position and another deletion/insertion/substitution is at position 369 in the amino acid sequence shown in SEQ ID NO:1 or at a position corresponding to this position. Preferably, such a variant has one or more substitutions, deletions and/or insertions in comparison to the corresponding sequence from which it is derived and wherein these substitutions, deletions and/or insertions occur at one or more of the positions corresponding to positions 2, 7, 54, 55, 58, 71, 72, 75, 76, 84, 88, 94, 98, 102, 105, 110, 111, 113, 116, 117, 119, 131, 135, 138, 139, 158, 159, 171, 173, 175, 177, 181, 189, 203, 208, 230, 231, 240, 247, 254, 255, 257, 269, 270, 291, 299, 305, 318, 349, 350, 357, 395, 364, 387 and 397.

Preferably, such a variant has the following substitutions in the amino acid sequence shown in SEQ ID NO:1 or at positions corresponding to these position: A112V-K152R-D199E-L367F.

In even more preferred embodiments, the variant according to the invention showing an improved activity in converting prenol into isoprene is characterized in that it has multiple mutations.

An alkenol dehydratase of the present invention can be fused to a homologous or heterologous polypeptide or protein, an enzyme, a substrate or a tag to form a fusion protein. Fusion proteins in accordance with the present invention will have the same improved activity as the alkenol dehydratase of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The present invention further relates to a nucleic acid molecule encoding an alkenol dehydratase of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

In addition, the present invention relates to a host cell comprising the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to a method for producing isoprene from prenol comprising the step of incubating an alkenol dehydratase of the invention with prenol under conditions allowing said conversion or comprising the step of culturing a host cell of the present invention in a suitable medium and recovering the produced isoprene.

It is also conceivable in this context that in such a method not only one enzyme according to the present invention is employed but a combination of two or more enzymes.

The present invention also relates to the use of an alkenol dehydratase variant or a host cell of the present invention as described above for the conversion of prenol into isoprene. Moreover, in a further embodiment, the present invention relates to a method for producing isoprene from prenol comprising the steps of: (i) culturing the above-described host cell of the invention in a suitable medium; and (ii) recovering the produced isoprene.

Thus, in a preferred embodiment, the present invention relates to methods and uses utilizing a host cell of the present invention wherein such a host cell is a recombinant organism in the sense that it is genetically modified due to the introduction of at least one nucleic acid molecule encoding an alkenol dehydratase variant as described above. Preferably, such a nucleic acid molecule is heterologous with regard to the organism which means that it does not naturally occur in said host cell.

In another preferred embodiment, such a host cell is an organism which is capable of producing prenol.

In another preferred embodiment the method according to the invention is carried out in culture, in the presence of an organism, preferably a microorganism, producing an enzyme variant of the present invention. In such an embodiment of the invention, an organism, preferably a microorganism, that produces an enzyme of the present invention is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro)organism is used having the natural or artificial property of endogenously producing prenol so as to produce isoprene directly from the substrate already present in the culture in solution.

In connection with the above described methods and uses, the microorganisms are cultivated under suitable culture conditions allowing the occurrence of the enzymatic reaction of the alkenol dehydratase variants of the present invention. The specific culture conditions depend on the specific microorganism employed but are well known to the person skilled in the art. The culture conditions are generally chosen in such a manner that they allow the expression of the genes encoding the alkenol dehydratases of the present invention. Various methods are known to the person skilled in the art in order to improve and fine-tune the expression of certain genes at certain stages of the culture such as induction of gene expression by chemical inducers or by a temperature shift.

The method according to the invention furthermore comprises the step of collecting gaseous products, i.e. isoprene, degassing out of the reaction, i.e. recovering the product which degasses, e.g., out of the culture. Thus, in a preferred embodiment, the method is carried out in the presence of a system for collecting isoprene under gaseous form during the reaction.

As a matter of fact, short alkenes such as isoprene adopt the gaseous state at room temperature and atmospheric pressure. Moreover, isoprene also adopts the gaseous state under culture conditions at 37° C. The method according to the invention therefore does not require extraction of isoprene from the liquid culture medium, a step which is always very costly when performed at industrial scale. The evacuation and storage of the gaseous hydrocarbons, in particular of isoprene, and their possible subsequent physical separation and chemical conversion can be performed according to any method known to one of skill in the art.

In yet a further embodiment, the method according to the invention can be carried out in vitro, e.g. in the presence of isolated enzyme or of cell lysates comprising the enzyme or partially purified enzyme preparations comprising the alkenol dehydratase variant of the present invention. In vitro preferably means in a cell-free system.

In one embodiment, the enzyme employed in the method is used in purified form. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of isoprene by using any detection system known to one of skill in the art such as gas chromatography or colorimetric tests for measuring the formation of isoprene.

In a particularly preferred embodiment of the invention the method is carried out in vitro and the enzyme is immobilized. Means and methods for immobilizing enzymes on different supports are well-known to the person skilled in the art.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

FIG. 1: Chemical structure of isoprene.

The invention will now be described by reference to the following examples which are merely illustrative and are not to be construed as a limitation of the scope of the present invention.

EXAMPLES

Example 1: Identification of Alkenol Dehydratase Enzyme Variants with Enhanced Activity in Converting Prenol into 1,3 Isoprene a) Rationale In order to identify residues improving the activity of the alkenol dehydratase (SEQ ID NO.1) for the conversion of prenol into isoprene, a library of mutants was designed, constructed and screened. The library was designed following the saturation mutagenesis principles, i.e. each of the 397 positions of the alkenol dehydratase is individually mutated in one of the 20 natural amino acids. According to this, the library presented a diversity of 7940 mutants.

b) Library Construction

A DNA library coding for single residue mutants of the alkenol dehydratase was constructed using standard mutagenesis techniques. The DNA library was based on the full-length coding sequence of the alkenol dehydratase enzyme, encoded by the amino acid sequence shown in SEQ ID NO: 1, with an N-term His6 tag. The sequence was subcloned into the commercial peT300:NT-DEST (Life technologies) expression vector and used as the template for the mutagenic PCR.

c) Screening Assay

This assay was set up as follows: The alkenol dehydratase point mutation DNA library in the pET25b+ expression vector was transformed into BL21(DE3) competent cells. Isolated clones were used to inoculate 0.3 ml of autoinduction medium (Studier F. W, Protein Expr. Purif. 41 (2005), 207-234) in deep well 96 well microplates, and grown overnight at 30° C. for 20-22 hours in a shaking incubator set at 700 rpm and 85% humidity. The cells were pelleted and stored at −80° C. overnight. These cell pellets that contain the expressed recombinant alkenol dehydratase variants were thawed on ice and resuspended in a reaction mix containing 50 mM Tris-Cl pH7.5, 25 mM KCl, 25 mM MgCl2, 4 mM DTT, 10 mM glutathione, supplemented with 0.25% Merck Novagen Lysonase, and 50 mM prenol (Sigma Aldrich). The reaction was incubated for 4 hours at 37° C., then for 16 hours at 20° C., and finally, stopped by a 5-minute incubation at 80° C.

The amount of isoprene produced was then quantified by gas chromatography analysis. For the GC headspace analysis, 100 µl of the headspace gas was injected in a Bruker GC450 system equipped with a Restek RT-Alumina Bond column (5 m×0.32 mm) and a Flame ionization detection system (FID). The GC analysis method used to detect isoprene is characterised by a constant oven temperature at 150° C., injector port temperature at 200° C. with a split ratio of 1:4 and the FID detector temperature at 250° C. Nitrogen was used as a carrier gas (constant flow of 1.20 ml/min) and a mixture of air (air flow 300 ml/min), nitrogen (28 ml/min flow) and hydrogen (flow of 30 ml/min) was used to supply the FID detection system.

d) Identification of Enzyme Variants with Increased Activity

The library of single residue variants of alkenol dehydratase was screened using the screening assay described above. About 72 clones were tested for each of the 397 randomized positions. A total number of 28584 variants were assayed. Alongside the alkenol dehydratase variants, control reactions were set up using either bacterial clones containing either the empty expression vector peT25b+ (negative control) or the expression vector expressing the wild type enzyme (positive control).

These variants were subjected to three consecutive rounds of screening. After primary screening, 703 variants displaying higher activity than the wt protein, were selected, and tested, in 8 replicates, in a second screening round.

Following secondary screening, 491 variants were subjected a third round of screening, also in 8 replicates, and in parallel, subjected to DNA sequencing in order to identify the mutation responsible for the change in enzyme activity. Most candidates were confirmed by tertiary screening, but sequencing showed that a significant fraction of them were identical, and that unexpected mutations were sometimes observed. Finally, a total of 104 different undescribed mutants with improved activity were identified.

Among these 104 mutants, 73 were simple mutants covering 39 different positions. These mutants are listed in Table 1, and the corresponding mutated positions in Table 2. In addition, 31 variants displaying multiple mutations, and having improved activity, were identified. These double mutants are listed in Table 3. Altogether, the mutations identified in the simple and multiple variants cover 58 positions of SEQ ID NO:1, as presented in Table 4.

TABLE 1

Single mutants of SEQ ID NO: 1 displaying improved activity of conversion of prenol into isoprene. The relative activity values correspond to the mean value of 8 replicates normalized by the activity of the wt. In addition, when a same single mutation was found in different clones, the relative activity value corresponds to the mean value of all replicates for all clones carrying the same mutation normalized by the activity of the wt.

| Mutated Position | Mutations | Relative activity vs wt |
|---|---|---|
| 54 | M54A | 1.45 |
| 54 | M54H | 1.77 |
| 55 | A55Y | 1.82 |
| 58 | A58S | 1.40 |
| 58 | A58T | 2.04 |
| 71 | S71Q | 2.92 |
| 72 | R72K | 2.63 |
| 75 | S75E | 1.63 |
| 76 | F76M | 2.09 |
| 76 | F76T | 1.46 |
| 84 | T84D | 1.25 |
| 84 | T84E | 1.78 |
| 94 | A94G | 1.65 |

TABLE 1-continued

Single mutants of SEQ ID NO: 1 displaying improved activity of conversion of prenol into isoprene. The relative activity values correspond to the mean value of 8 replicates normalized by the activity of the wt. In addition, when a same single mutation was found in different clones, the relative activity value corresponds to the mean value of all replicates for all clones carrying the same mutation normalized by the activity of the wt.

| Mutated Position | Mutations | Relative activity vs wt |
|---|---|---|
| 98 | Y98L | 1.85 |
| 102 | S102F | 1.61 |
| 111 | R111I | 2.17 |
| 111 | R111N | 2.02 |
| 111 | R111S | 2.06 |
| 111 | R111T | 1.97 |
| 111 | R111V | 2.49 |
| 112 | A112I | 4.33 |
| 112 | A112L | 2.68 |
| 112 | A112N | 4.93 |
| 112 | A112V | 4.93 |
| 116 | H116A | 2.33 |
| 119 | D119N | 2.57 |
| 119 | D119T | 1.97 |
| 131 | W131Y | 1.47 |
| 135 | E135I | 1.78 |
| 135 | E135K | 1.71 |
| 135 | E135L | 1.70 |
| 135 | E135R | 1.51 |
| 138 | G138A | 1.67 |
| 138 | G138D | 1.84 |
| 138 | G138L | 1.77 |
| 138 | G138M | 1.65 |
| 138 | G138N | 1.69 |
| 138 | G138S | 1.68 |
| 158 | M158L | 1.72 |
| 159 | Y159L | 2.11 |
| 171 | Y171F | 2.88 |
| 175 | H175M | 2.59 |
| 181 | I181H | 2.01 |
| 189 | N189H | 2.17 |
| 199 | D199W | 2.78 |
| 203 | V203I | 3.03 |
| 203 | V203T | 2.12 |
| 208 | V208P | 2.07 |
| 230 | A230P | 2.05 |
| 231 | W231Y | 2.65 |
| 240 | I240G | 1.93 |
| 240 | I240L | 1.64 |
| 240 | I240Q | 2.11 |
| 240 | I240R | 3.04 |
| 240 | I240T | 1.64 |
| 240 | I240W | 2.61 |
| 240 | I240Y | 2.41 |
| 247 | F247A | 1.72 |
| 247 | F247W | 1.83 |
| 254 | E254N | 1.88 |
| 254 | E254S | 2.46 |
| 255 | S255I | 3.18 |
| 257 | A257L | 3.40 |
| 257 | A257V | 2.32 |
| 269 | W269C | 3.08 |
| 269 | W269S | 3.95 |
| 269 | W269T | 2.58 |
| 269 | W269V | 2.85 |
| 270 | T270L | 2.76 |
| 305 | V305L | 1.63 |
| 318 | V318C | 1.44 |
| 367 | L367M | 1.69 |

TABLE 2

Positions of SEQ ID NO: 1 for which single mutations improving activity of conversion of prenol into isoprene have been identified.

Positions 54
55
58
71
72
75
76
84
94
98
102
111
112
116
119
131
135
138
158
159
171
175
181
189
199
203
208
230
231
240
247
254
255
257
269
270
305
318
367

TABLE 3

Double mutants of SEQ ID NO: 1 displaying improved activity of conversion of prenol into isoprene. The relative activity values correspond to the mean value of 8 replicates normalized by the activity of the wt. In addition, when the same mutations were found in different clones, the relative activity value corresponds to the mean value of all replicates for all clones carrying the same mutations normalized by the activity of the wt.

| Mutations | Relative activity vs wt |
|---|---|
| A112L-K350Q | 2.55 |
| A112V-K350L | 4.85 |
| A173S-I181L | 2.08 |
| A173T-I181L | 2.14 |
| A173V-V318A | 1.94 |
| D119H-S357A | 2.82 |
| D119R-S357M | 1.83 |
| E135I-V318A | 1.59 |
| F76V-E77L | 2.67 |
| G132S-V318S | 2.37 |
| H116Y-D117N | 2.19 |
| K126F-G364M | 2.20 |
| L105A-L113T | 1.85 |
| L105N-L113T | 1.61 |
| L105Q-A112T | 2.37 |
| L110V-A112T | 2.57 |
| L113T-H177G | 1.51 |
| M387V-A395D | 2.46 |
| M387V-A395S | 2.27 |
| R111G-A349S | 2.09 |

TABLE 3-continued

Double mutants of SEQ ID NO: 1 displaying improved activity of conversion of prenol into isoprene. The relative activity values correspond to the mean value of 8 replicates normalized by the activity of the wt. In addition, when the same mutations were found in different clones, the relative activity value corresponds to the mean value of all replicates for all clones carrying the same mutations normalized by the activity of the wt.

| Mutations | Relative activity vs wt |
|---|---|
| R111L-D119S | 2.58 |
| R2C-I240E | 1.33 |
| S75M-Q291W | 1.78 |
| T7V-I181S | 2.63 |
| V88T-K152R | 1.56 |
| Y159L-K397Q | 2.29 |
| Y98L-E299D | 1.89 |
| Y98M-Q291E | 1.78 |
| D119R-K350G-S357L | 2.20 |

TABLE 4

Positions of SEQ ID NO: 1 for which mutations improving activity of conversion of prenol into isoprene have been identified in all the variants.

Positions mutated in all variants 2
7
54
55
58
71
72
75
76
84
88
94
98
102
105
110
111
112
113
116
117
119
131
135
138
158
159
171
173
175
177
181
189
199
203
208
230
231
240
247
254
255
257
269
270
291
299
305
318
349

TABLE 4-continued

Positions of SEQ ID NO: 1 for which mutations improving activity of conversion of prenol into isoprene have been identified in all the variants. Positions mutated in all variants 350
357
364
367
387
395
397

Example 2: Identification of Alkenol Dehydratase Enzyme Variants with Further Enhanced Activity in Converting Prenol into 1,3 Isoprene In order to further improve the activity of the alkenol dehydratase (SEQ ID NO.1) for the conversion of prenol into isoprene, new libraries of multiple mutants were designed, constructed and screened. In contrast to the previous libraries, these new libraries were screened against a low concentration of prenol (1 mM) in order to allow for new mutations to be identified.

This assay was set up as follows: The alkenol dehydratase point mutation DNA library in the pET25b+ expression vector was transformed into BL21(DE3) competent cells. Isolated clones were used to inoculate 0.3 ml of autoinduction medium (Studier F. W, Protein Expr. Purif. 41 (2005), 207-234) in deep well 96 well microplates, and grown overnight at 30° C. for 20-22 hours in a shaking incubator set at 700 rpm and 85% humidity. The cells were pelleted and stored at −80° C. overnight. These cell pellets containing the expressed recombinant alkenol dehydratase variants were thawed on ice and resuspended in a reaction mix containing 50 mM Tris-CI pH7.5, 150 mM KCl, 2 mM MgCl$_2$, and 1 mM prenol (Sigma Aldrich). The reaction was incubated for 2 hours at 37° C. and finally, stopped by a 3-minute incubation at 80° C.

The amount of isoprene produced was then quantified by gas chromatography analysis. For the GC headspace analysis, 100 µl of the headspace gas was injected in a Bruker GC450 system equipped with a Restek RT-Alumina Bond column (5 m×0.32 mm) and a Flame ionization detection system (FID). The GC analysis method used to detect isoprene is characterised by a constant oven temperature at 150° C., injector port temperature at 200° C. with a split ratio of 1:4 and the FID detector temperature at 250° C. Nitrogen was used as a carrier gas (constant flow of 1.20 ml/min) and a mixture of air (air flow 300 ml/min), nitrogen (28 ml/min flow) and hydrogen (flow of 30 ml/min) was used to supply the FID detection system.

A total of 20 new mutants were thus identified which are summarized in Table 5.

TABLE 5

Multiple mutants of SEQ ID NO. 1 displaying improved activity in the conversion of prenol into isoprene. The relative activity values correspond to the mean value of 8 replicates normalized by the activity of the wt. In addition, when a same set of multiple mutations were found in different clones, the relative activity value corresponds to the mean value of all replicates for all clones carrying the same mutations normalized by the activity of the wt.

| Mutations | Improvement factor/wt |
| --- | --- |
| R72P-V195F-Y251M-W269A | 65.1 |
| R72P-Y251M-W269A | 51.5 |
| A112V-V195F-W269A | 50.8 |
| R72P-W269A | 49.7 |
| V195F-Y251M-W269A | 46.7 |
| V195F-D199E-W269A | 44.3 |
| A112V-Y251M-W269A | 41.4 |
| D199E-W269A | 40.4 |
| S75A-Y251M-W269A | 39.9 |
| A112V-Y251N-W269A | 36.9 |
| A112V-V195F-W269A | 36.8 |
| R72P-S75A-Y251M | 34.1 |
| S75A-K152R-L367F | 30.9 |
| K152R-Y171F-E254G-L367F | 25.6 |
| S75A-Y171F-D199E-L367F | 22.7 |
| S71A-S75A | 21.3 |
| S71A-D119Q-L367F | 20.4 |
| D119Q-Y171F-E254G-L367F | 19.6 |
| A112V-K152R-D199E-L367F | 19.0 |
| S71N-E135T | 18.5 |

The invention claimed is:

1. An alkenol dehydratase variant showing an improved activity in converting prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions: 2, 7, 54, 55, 58, 88, 94, 105, 110, 111, 112, 113, 117, 139, 171, 177, 189, 203, 208, 231, 240, 257, 270, 291, 299, 305, 349, 350, 395 and 397 in the amino acid sequence at least 85% identical to the sequence of SEQ ID NO:1.

2. The alkenol dehydratase variant of claim 1 having an amino acid sequence as shown in SEQ ID NO:1 or an amino acid sequence having at least 90% sequence identity to SEQ ID NO:1, in which one or more amino acid residues at a position selected from the group consisting of positions 2, 7, 54, 55, 58, 88, 94, 105, 110, 111, 112, 113, 117, 139, 171, 177, 189, 203, 208, 231, 240, 257, 270, 291, 299, 305, 349, 350, 395 and 397 in the amino acid sequence shown in SEQ ID NO:1 or at a position corresponding to any of these positions, are substituted with another amino acid residue or deleted or wherein an insertion has been effected at one or more of these positions and wherein said alkenol dehydratase has an improved activity in converting prenol into isoprene.

3. The alkenol dehydratase variant of claim 1, wherein
  (1) an amino acid residue at position 2 in the amino acid sequence shown in SEQ ID NO:1 or at a position corresponding to this position, is deleted or substituted with cysteine; and/or (2) an amino acid residue at position 7 in the amino acid sequence shown in SEQ ID NO:1 or at a position corresponding to this position, is deleted or substituted with valine; and/or
(3) an amino acid residue at position 54 in the amino acid sequence shown in SEQ ID NO:1 or at a position corresponding to this position, is deleted or substituted with alanine or histidine; and/or
(4) an amino acid residue at position 55 in the amino acid sequence shown in SEQ ID NO:1 or at a position corresponding to this position, is deleted or substituted with tyrosine; and/or
(5) an amino acid residue at position 58 in the amino acid sequence shown in SEQ ID NO:1 or at a position corresponding to this position, is deleted or substituted with serine or threonine; and/or
(6) an amino acid residue at position 88 in the amino acid sequence shown in SEQ ID NO:1 or at a position corresponding to this position, is deleted or substituted with threonine; and/or
(7) an amino acid residue at position 94 in the amino acid sequence shown in SEQ ID NO:1 or at a position corresponding to this position, is deleted or substituted with glycine; and/or
(8) an amino acid residue at position 105 in the amino acid sequence shown in SEQ ID NO:1 or at a position corresponding to this position, is deleted or substituted with alanine, glutamine or asparagine; and/or
(9) an amino acid residue at position 110 in the amino acid sequence shown in SEQ ID NO:1 or at a position corresponding to this position, is deleted or substituted with valine; and/or
(10) an amino acid residue at position 111 in the amino acid sequence shown in SEQ ID NO:1 or at a position corresponding to this position, is deleted or substituted with glycine, leucine, isoleucine, asparagine, serine, threonine, or valine; and/or
(11) an amino acid residue at position 112 in the amino acid sequence shown in SEQ ID NO:1 or at a position corresponding to this position, is deleted or substituted with isoleucine, leucine, asparagine, threonine or valine; and/or
(12) an amino acid residue at position 113 in the amino acid sequence shown in SEQ ID NO:1 or at a position corresponding to this position, is deleted or substituted with threonine; and/or
(13) an amino acid residue at position 117 in the amino acid sequence shown in SEQ ID NO:1 or at a position corresponding to this position, is deleted or substituted with asparagine; and/or
(14) an amino acid residue at position 139 in the amino acid sequence shown in SEQ ID NO:1 or at a position corresponding to this position, is deleted or substituted with tyrosine; and/or
(15) an amino acid residue at position 171 in the amino acid sequence shown in SEQ ID NO:1 or at a position corresponding to this position, is deleted or substituted with phenylalanine; and/or
(16) an amino acid residue at position 177 in the amino acid sequence shown in SEQ ID NO:1 or at a position corresponding to this position, is deleted or substituted with glycine; and/or
(17) an amino acid residue at position 189 in the amino acid sequence shown in SEQ ID NO:1 or at a position corresponding to this position, is deleted or substituted with histidine; and/or
(18) an amino acid residue at position 203 in the amino acid sequence shown in SEQ ID NO:1 or at a position corresponding to this position, is deleted or substituted with isoleucine or threonine; and/or
(19) an amino acid residue at position 208 in the amino acid sequence shown in SEQ ID NO:1 or at a position corresponding to this position, is deleted or substituted with proline; and/or
(20) an amino acid residue at position 231 in the amino acid sequence shown in SEQ ID NO:1 or at a position corresponding to this position, is deleted or substituted with tyrosine; and/or
(21) an amino acid residue at position 240 in the amino acid sequence shown in SEQ ID NO:1 or at a position corresponding to this position, is deleted or substituted with glycine, leucine, glutamine, arginine, threonine, tryptophan or tyrosine; and/or
(22) an amino acid residue at position 257 in the amino acid sequence shown in SEQ ID NO:1 or at a position corresponding to this position, is deleted or substituted with leucine or valine; and/or
(23) an amino acid residue at position 270 in the amino acid sequence shown in SEQ ID NO:1 or at a position corresponding to this position, is deleted or substituted with leucine; and/or
(24) an amino acid residue at position 291 in the amino acid sequence shown in SEQ ID NO:1 or at a position corresponding to this position, is deleted or substituted with tryptophan or glutamic acid; and/or
(25) an amino acid residue at position 299 in the amino acid sequence shown in SEQ ID NO:1 or at a position corresponding to this position, is deleted or substituted with aspartic acid; and/or
(26) an amino acid residue at position 305 in the amino acid sequence shown in SEQ ID NO:1 or at a position corresponding to this position, is deleted or substituted with leucine; and/or
(27) an amino acid residue at position 349 in the amino acid sequence shown in SEQ ID NO:1 or at a position corresponding to this position, is deleted or substituted with serine; and/or
(28) an amino acid residue at position 350 in the amino acid sequence shown in SEQ ID NO:1 or at a position corresponding to this position, is deleted or substituted with glycine, glutamine or leucine; and/or
(29) an amino acid residue at position 395 in the amino acid sequence shown in SEQ ID NO:1 or at a position corresponding to this position, is deleted or substituted with aspartic acid or serine; and/or
(30) an amino acid residue at position 397 in the amino acid sequence shown in SEQ ID NO:1 or at a position corresponding to this position, is deleted or substituted with glutamine.

4. An alkenol dehydratase variant showing an improved activity in converting prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 71, 72, 75, 76, 84, 98, 102, 116, 119, 131, 135, 138, 158, 159, 173, 175, 181, 199, 230, 247, 254, 255, 269, 318, 357, 364, 367 and 387 in the amino acid sequence at least 85% identical to the sequence of SEQ ID NO:1, wherein (1) an amino acid residue at position 71 in the amino acid sequence shown in SEQ ID NO:1 or at a position corresponding to this position, is deleted or substituted with glutamine, alanine or asparagine; and/or
(2) an amino acid residue at position 72 in the amino acid sequence shown in SEQ ID NO:1 or at a position corresponding to this position, is deleted or substituted with lysine or proline; and/or
(3) an amino acid residue at position 75 in the amino acid sequence shown in SEQ ID NO:1 or at a position corresponding to this position, is deleted or substituted with glutamic acid, alanine or methionine; and/or
(4) an amino acid residue at position 76 in the amino acid sequence shown in SEQ ID NO:1 or at a position corresponding to this position, is deleted or substituted with methionine, valine or threonine; and/or
(5) an amino acid residue at position 84 in the amino acid sequence shown in SEQ ID NO:1 or at a position corresponding to this position, is deleted or substituted with aspartic acid or glutamic acid; and/or
(6) an amino acid residue at position 98 in the amino acid sequence shown in SEQ ID NO:1 or at a position corresponding to this position, is deleted or substituted with leucine or methionine; and/or
(7) an amino acid residue at position 102 in the amino acid sequence shown in SEQ ID NO:1 or at a position corresponding to this position, is deleted or substituted with phenylalanine; and/or
(8) an amino acid residue at position 116 in the amino acid sequence shown in SEQ ID NO:1 or at a position corresponding to this position, is deleted or substituted with alanine or tyrosine; and/or
(9) an amino acid residue at position 119 in the amino acid sequence shown in SEQ ID NO:1 or at a position corresponding to this position, is deleted or substituted with arginine, histidine, serine, threonine, glutamine or asparagine; and/or
(10) an amino acid residue at position 131 in the amino acid sequence shown in SEQ ID NO:1 or at a position corresponding to this position, is deleted or substituted with tyrosine; and/or
(11) an amino acid residue at position 135 in the amino acid sequence shown in SEQ ID NO:1 or at a position corresponding to this position, is deleted or substituted with isoleucine, lysine, leucine, threonine or arginine; and/or
(12) an amino acid residue at position 138 in the amino acid sequence shown in SEQ ID NO:1 or at a position corresponding to this position, is deleted or substituted with alanine, aspartic acid, leucine, methionine, asparagine, or serine; and/or
(13) an amino acid residue at position 158 in the amino acid sequence shown in SEQ ID NO:1 or at a position corresponding to this position, is deleted or substituted with leucine; and/or
(14) an amino acid residue at position 159 in the amino acid sequence shown in SEQ ID NO:1 or at a position corresponding to this position, is deleted or substituted with leucine; and/or
(15) an amino acid residue at position 173 in the amino acid sequence shown in SEQ ID NO:1 or at a position corresponding to this position, is deleted or substituted with serine, threonine or valine; and/or
(16) an amino acid residue at position 175 in the amino acid sequence shown in SEQ ID NO:1 or at a position corresponding to this position, is deleted or substituted with methionine; and/or
(17) an amino acid residue at position 181 in the amino acid sequence shown in SEQ ID NO:1 or at a position corresponding to this position, is deleted or substituted with histidine, serine or leucine; and/or
(18) an amino acid residue at position 199 in the amino acid sequence shown in SEQ ID NO:1 or at a position corresponding to this position, is deleted or substituted with tryptophan or glutamic acid; and/or
(19) an amino acid residue at position 230 in the amino acid sequence shown in SEQ ID NO:1 or at a position corresponding to this position, is deleted or substituted with proline; and/or
(20) an amino acid residue at position 247 in the amino acid sequence shown in SEQ ID NO:1 or at a position corresponding to this position, is deleted or substituted with alanine or tryptophan; and/or
(21) an amino acid residue at position 254 in the amino acid sequence shown in SEQ ID NO:1 or at a position corresponding to this position, is deleted or substituted with asparagine, glycine or serine; and/or
(22) an amino acid residue at position 255 in the amino acid sequence shown in SEQ ID NO:1 or at a position corresponding to this position, is deleted or substituted with isoleucine; and/or
(23) an amino acid residue at position 269 in the amino acid sequence shown in SEQ ID NO:1 or at a position corresponding to this position, is deleted or substituted with cysteine, serine, threonine, alanine or valine; and/or
(24) an amino acid residue at position 318 in the amino acid sequence shown in SEQ ID NO:1 or at a position corresponding to this position, is deleted or substituted with alanine, cysteine or serine; and/or
(25) an amino acid residue at position 357 in the amino acid sequence shown in SEQ ID NO:1 or at a position corresponding to this position, is deleted or substituted with alanine, leucine or methionine; and/or
(26) an amino acid residue at position 364 in the amino acid sequence shown in SEQ ID NO:1 or at a position corresponding to this position, is deleted or substituted with methionine; and/or
(27) an amino acid residue at position 367 in the amino acid sequence shown in SEQ ID NO:1 or at a position corresponding to this position, is deleted or substituted with methionine or phenylalanine; and/or
(28) an amino acid residue at position 387 in the amino acid sequence shown in SEQ ID NO:1 or at a position corresponding to this position, is deleted or substituted with valine.

5. The alkenol dehydratase variant of claim 4 showing an improved activity in converting prenol into isoprene over the corresponding alkenol dehydratase from which it is derived, wherein the alkenol dehydratase variant has an amino acid sequence as shown in SEQ ID NO:1 or an amino acid sequence having at least 90% sequence identity to SEQ ID NO:1, in which one or more amino acid residues at a position selected from 71, 72, 75, 76, 84, 98, 102, 116, 119, 131, 135, 138, 158, 159, 173, 175, 181, 199, 230, 247, 254, 255, 269, 318, 357, 364, 367 and 387 in the amino acid sequence shown in SEQ ID NO:1 or at a position corresponding to any of these positions, are substituted with another amino acid residue or deleted or wherein an insertion has been effected at one or more of these positions and wherein said alkenol dehydratase has an improved activity in converting prenol into isoprene, wherein (1) an amino acid residue at position 71 in the amino acid sequence shown in SEQ ID NO:1 or at a position corresponding to this position, is deleted or substituted with glutamine, alanine or asparagine; and/or (2) an amino acid residue at position 72 in the amino acid sequence shown in SEQ ID NO:1 or at a position corresponding to this position, is deleted or substituted with lysine or proline; and/or (3) an amino acid residue at position 75 in the amino acid sequence shown in SEQ ID NO:1 or at a position corresponding to this position, is deleted or substituted with glutamic acid, alanine or methionine; and/or (4) an amino acid residue at position 76 in the amino acid sequence shown in SEQ ID NO:1 or at a position corresponding to this position, is deleted or substituted with methionine, valine or threonine; and/or (5) an amino acid residue at position 84 in the amino acid sequence shown in SEQ ID NO:1 or at a position corresponding to this position, is deleted or substituted with aspartic acid or glutamic acid; and/or (6) an amino acid residue at position 98 in the amino acid sequence shown in SEQ ID NO:1 or at a position corresponding to this position, is deleted or substituted with leucine or methionine; and/or (7) an amino acid residue at position 102 in the amino acid sequence shown in SEQ ID NO:1 or at a position corresponding to this position, is deleted or substituted with phenylalanine; and/or (8) an amino acid residue at position 116 in the amino acid sequence shown in SEQ ID NO:1 or at a position corresponding to this position, is deleted or substituted with alanine or tyrosine; and/or (9) an amino acid residue at position 119 in the amino acid sequence shown in SEQ ID NO:1 or at a position corresponding to this position, is deleted or substituted with arginine, histidine, serine, threonine, alanine, glutamine or asparagine; and/or

(10) an amino acid residue at position 131 in the amino acid sequence shown in SEQ ID NO:1 or at a position corresponding to this position, is deleted or substituted with asparagine, serine or tyrosine; and/or

(11) an amino acid residue at position 135 in the amino acid sequence shown in SEQ ID NO:1 or at a position corresponding to this position, is deleted or substituted with isoleucine, lysine, leucine, threonine or alanine; and/or

(12) an amino acid residue at position 138 in the amino acid sequence shown in SEQ ID NO:1 or at a position corresponding to this position, is deleted or substituted with alanine, aspartic acid, leucine, methionine, asparagine, or serine; and/or

(13) an amino acid residue at position 158 in the amino acid sequence shown in SEQ ID NO:1 or at a position corresponding to this position, is deleted or substituted with leucine; and/or

(14) an amino acid residue at position 159 in the amino acid sequence shown in SEQ ID NO:1 or at a position corresponding to this position, is deleted or substituted with leucine; and/or

(15) an amino acid residue at position 173 in the amino acid sequence shown in SEQ ID NO:1 or at a position corresponding to this position, is deleted or substituted with serine, threonine or valine; and/or

(16) an amino acid residue at position 175 in the amino acid sequence shown in SEQ ID NO:1 or at a position corresponding to this position, is deleted or substituted with methionine; and/or

(17) an amino acid residue at position 181 in the amino acid sequence shown in SEQ ID NO:1 or at a position corresponding to this position, is deleted or substituted with histidine, serine or leucine; and/or

(18) an amino acid residue at position 199 in the amino acid sequence shown in SEQ ID NO:1 or at a position corresponding to this position, is deleted or substituted with tryptophan; and/or

(19) an amino acid residue at position 230 in the amino acid sequence shown in SEQ ID NO:1 or at a position corresponding to this position, is deleted or substituted with proline; and/or

(20) an amino acid residue at position 247 in the amino acid sequence shown in SEQ ID NO:1 or at a position corresponding to this position, is deleted or substituted with alanine or tryptophan; and/or

(21) an amino acid residue at position 254 in the amino acid sequence shown in SEQ ID NO:1 or at a position corresponding to this position, is deleted or substituted with asparagine, glycine or serine; and/or

(22) an amino acid residue at position 255 in the amino acid sequence shown in SEQ ID NO:1 or at a position corresponding to this position, is deleted or substituted with isoleucine; and/or

(23) an amino acid residue at position 269 in the amino acid sequence shown in SEQ ID NO:1 or at a position corresponding to this position, is deleted or substituted with cysteine, serine, threonine, alanine or valine; and/or

(24) an amino acid residue at position 318 in the amino acid sequence shown in SEQ ID NO:1 or at a position corresponding to this position, is deleted or substituted with alanine, cysteine or serine; and/or

(25) an amino acid residue at position 357 in the amino acid sequence shown in SEQ ID NO:1 or at a position corresponding to this position, is deleted or substituted with alanine, leucine or methionine; and/or

(26) an amino acid residue at position 364 in the amino acid sequence shown in SEQ ID NO:1 or at a position corresponding to this position, is deleted or substituted with methionine; and/or

(27) an amino acid residue at position 367 in the amino acid sequence shown in SEQ ID NO:1 or at a position corresponding to this position, is deleted or substituted with methionine or phenylalanine; and/or

(28) an amino acid residue at position 387 in the amino acid sequence shown in SEQ ID NO:1 or at a position corresponding to this position, is deleted or substituted with valine.

6. A nucleic acid molecule encoding the alkenol dehydratase variant of claim 1.

7. A vector comprising the nucleic acid molecule of claim 6.

8. A host cell comprising the vector of claim 7.

9. A method for producing isoprene from prenol comprising the steps of:
  incubating an alkenol dehydratase variant of claim 1 with prenol, wherein the prenol is enzymatically converted into isoprene; and
  (ii) recovering the produced isoprene.

10. The method of claim 9 wherein the enzymatic conversion of prenol into isoprene is carried out in a host cell comprising an alkenol dehydratase variant.

11. The method of claim 9, wherein the enzymatic conversion is carried out in vitro.

12. The method of claim 10 wherein the host cell is capable of producing prenol.

* * * * *

UNITED STATES PATENT AND TRADEMARK OFFICE
CERTIFICATE OF CORRECTION

PATENT NO. : 10,113,186 B2  
APPLICATION NO. : 15/526248  
DATED : October 30, 2018  
INVENTOR(S) : Sabine Mazaleyrat, Marc Delcourt and Philippe Marlière Page 1 of 1

It is certified that error appears in the above-identified patent and that said Letters Patent is hereby corrected as shown below:

In the Claims

Column 52, Lines 53-58, Claim 9 should read:
--A method for producing isoprene from prenol comprising the steps of:
    (i) incubating an alkenol dehydratase variant of claim 1 with prenol, wherein the prenol is enzymatically converted into isoprene; and
    (ii) recovering the produced isoprene.--

Signed and Sealed this
Twenty-seventh Day of August, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 397
<212> TYPE: PRT
<213> ORGANISM: Castellaniella defragrans

<400> SEQUENCE: 1

Met Arg Phe Thr Leu Lys Thr Thr Ala Ile Val Ser Ala Ala Ala Leu
1               5                   10                  15

Leu Ala Gly Phe Gly Pro Pro Pro Arg Ala Ala Glu Leu Pro Pro Gly
                20                  25                  30

Arg Leu Ala Thr Thr Glu Asp Tyr Phe Ala Gln Gln Ala Lys Gln Ala
            35                  40                  45

Val Thr Pro Asp Val Met Ala Gln Leu Ala Tyr Met Asn Tyr Ile Asp
        50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr

```
                          85                  90                  95
Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
            130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
            210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
                260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
            290                 295                 300

Val Arg Glu Thr Ala Gly Thr Asp Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
            370                 375                 380

Leu Arg Met Pro Pro Pro Ala Ala Lys Leu Ala Gly Lys
385                 390                 395
```